(12) United States Patent
Guelcher et al.

(10) Patent No.: US 9,950,096 B2
(45) Date of Patent: Apr. 24, 2018

(54) PARTICLE/POLYURETHANE COMPOSITES AND METHODS THEREOF

(75) Inventors: Scott A. Guelcher, Franklin, TN (US); Edna Margarita Prieto, Nashville, TN (US); Jerald E. Dumas, Atlanta, GA (US); Katarzyna Jadwiga Zienkiewicz, Nashville, TN (US); Jonathan Page, Mount Juliet, TN (US)

(73) Assignee: Vanderbilt University, Nashville, TN (US)

(*) Notice: Subject to any disclaimer, the term of this patent is extended or adjusted under 35 U.S.C. 154(b) by 1411 days.

(21) Appl. No.: 13/005,528

(22) Filed: Jan. 12, 2011

(65) Prior Publication Data

US 2011/0237704 A1 Sep. 29, 2011

Related U.S. Application Data

(60) Provisional application No. 61/294,466, filed on Jan. 12, 2010.

(51) Int. Cl.
| | |
|---|---|
| *A61L 27/46* | (2006.01) |
| *A61L 27/44* | (2006.01) |
| *A61L 27/48* | (2006.01) |
| *A61L 27/54* | (2006.01) |
| *A61L 27/56* | (2006.01) |

(52) U.S. Cl.
CPC .......... *A61L 27/46* (2013.01); *A61L 27/446* (2013.01); *A61L 27/48* (2013.01); *A61L 27/54* (2013.01); *A61L 27/56* (2013.01); *A61L 2300/406* (2013.01)

(58) Field of Classification Search
CPC ....................................................... A61L 27/46
See application file for complete search history.

(56) References Cited

U.S. PATENT DOCUMENTS

| | | | | |
|---|---|---|---|---|
| 2005/0013793 | A1* | 1/2005 | Beckman | C08G 18/12 424/78.27 |
| 2006/0216323 | A1* | 9/2006 | Knaack | A61K 31/785 424/422 |
| 2007/0191567 | A1* | 8/2007 | Tsuge | C08G 18/10 528/44 |
| 2010/0112032 | A1* | 5/2010 | Guelcher | A61L 27/44 424/423 |

\* cited by examiner

*Primary Examiner* — Michael Pepitone
(74) *Attorney, Agent, or Firm* — Stites & Harbison PLLC; Sean P. Richie

(57) ABSTRACT

The present invention encompasses the finding that certain treatments (e.g., surface modifications) to particulate materials can provide surprising and unexpected benefits and/or features to composites and/or compositions as described herein. In some embodiments, such benefits and/or features may render particular composites and/or compositions particularly useful in a certain therapeutic context (e.g, for repair of tibial plateau, femoral head, craniofacial, or lateral mandibular body defects). The present invention demonstrates that certain composites and/or compositions wherein the particular material is or comprises defatted bone have surprising and beneficial attributes.

44 Claims, 20 Drawing Sheets

PARTICLE/POLYURETHANE COMPOSITES AND METHODS THEREOF

CROSS REFERENCES OF RELATED APPLICATIONS

The present application claims priority under 35 U.S.C. § 119(e) to U.S. provisional patent applications, U.S. Ser. No. 61/294,466, filed Jan. 12, 2010, which is incorporated herein by reference.

GOVERNMENT SUPPORT

This invention was made with support from the United State Department of Defense Grant numbers W81XWH-08-2-0034 and W81XWH-04-2-0031 through a sub-contract with Rutgers University to Vanderbilt University and from the National Science Foundation Grant Number DMR-0847711. The United States Government has certain rights to this invention.

BACKGROUND

Bone is the second most commonly transplanted tissue after blood (Giannoudis P, Dinopoulos H, Tsiridis E. Bone substitutes: An update. Injury, Int. J. Care Injured 2005; 36S:S20) with around 2.2 million grafting procedures performed worldwide each year (Lewandrowski K, Gresser J, Wise D, Trantol D. Bioresorbable bone graft substitutes of different osteoconductivities: a histologic evaluation of osteointegration of poly(propylene glycol-co-fumaric acid)-based cement implants in rats. Biomaterials 2000; 21:757; Van der Stok J, Van Lieshout E M M, El-Massoudi Y, Van Kralingen G H, Patka P. Bone substitutes in the Netherlands—A systematic literature review. Acta Biomaterialia 2010, In Press). Although autologous bone remains the standard of care for treatment of bone defects synthetic bone grafts have been developed to address the clinical drawbacks imposed by the harvesting procedure of autografts. Ceramic biomaterials such as calcium phosphate cements offer biocompatibility and osteoconductivity but have brittle mechanical properties (Kretlow JD, Young S, Klouda L, Wong M, Mikos A G. Injectable Biomaterials for Regenerating Complex Craniofacial Tissues. Adv Mater. 2009; 21:3368), can migrate from the implant site, and have slow resorption rates (Gilardino M, Cabiling D, Bartlett S. Long-term follow-up experience with carbonated calcium phosphate cement (Norian) for cranioplasty in children and adults. Plast Reconstr Surg. 2009; 123:983). Polymeric materials such as poly(methyl methacrylate) (PMMA) can be injected into the defect. However, PMMA polymerizes at high temperatures causing tissue necrosis, and generates stress-shielding which accelerates resorption of the neighboring bone (Ni G, Lu W, Chiu P, Wang Y, Li Z, Zhang Y, Xu B, Deng L, Luk K. Mechanical properties of femoral cortical bone following cemented hip replacement. Journal of Orthopaedic Research 2007; 25:1408). Polyurethane (PUR) networks from lysine polyisocyanates have been shown to support cellular proliferation and differentiation (Guelcher S A, Srinivasan A, Dumas J E, Didier J E, McBride S, Hollinger J O. Synthesis, mechanical properties, biocompatibility, and biodegradation of polyurethane networks from lysine polyisocyanates. Biomaterials 2008; 29:1762), to function as injectable delivery systems and to degrade to non-cytotoxic compounds (Hafeman A, Li B, Toshikata Y, Zienkiewicz K, Davidson J M, Guelcher S A. Injectable Biodegradable Polyurethane Scaffolds with Release of Platelet-derived Growth Factor for Tissue Repair and Regeneration. Pharmaceutical Research 2008; 25:23877).

Efforts have been made to develop composites comprising polyurethane materials combined with particulates (e.g., bone particles and ceramic biomaterials such as calcium phosphate). For example, bone particles incorporated in polyurethane materials can act as a reinforcement material as well as a porogen that guides cellular infiltration.

Interfacial binding and particulates loading are both critical to mechanical properties and cellular infiltration rates. The present application discloses that composite materials with covalent bonding between particulates (e.g., bone particles and ceramic biomaterials such as calcium phosphate) and polyurethane materials, and/or high particulate content show increased mechanical properties while preserving osteoconductive biological properties. Inventive compositions (e.g., composites) described here can be utilized in various orthopedic applications.

SUMMARY

The invention relates to injectable and/or moldable composites and/or compositions that comprise a particulate material and a polyurethane material. The invention provides certain such composites and/or compositions, and also making and using such composites and/or compositions, for example in medicine, for example in orthopedic applications. Related compositions and methods are also provided.

Among other things, the present invention encompasses the finding that certain treatments (e.g., surface modifications) to particulate materials can provide surprising and unexpected benefits and/or features to composites and/or compositions as described herein. In some embodiments, such benefits and/or features may render particular composites and/or compositions particularly useful in a certain therapeutic context (e.g, for repair of tibial plateau, femoral head, craniofacial, or lateral mandibular body defects).

Among other things, the present invention demonstrates that certain composites and/or compositions wherein the particular material is or comprises defatted bone have surprising and beneficial attributes. Without wishing to be bound by any particular theory, the present invention encompasses the recognition that defatted bone particles may show improved interactions with polyurethane materials, and that such improved interactions may contributed to one or more of the observed surprising and beneficial attributes. In some embodiments, the present invention provides composites and/or compositions comprising defatted bone particulates and a polyurethane material, in which covalent bones are or can be formed between the particulates and the polyurethane material. In some embodiments, provided compositions comprise defatted bone particles that have a specific reaction rate relative to water of 5-7 g mol$^{-1}$ sec$^{-1}$ at 23° C. In some embodiments, a relative kinetic rate for reaction with isocyanate prepolymers (defined by the kinetic rate of a particulate component divided by that of a polyol) in a composition is about 0.1-0.6.

Among other things, the present invention demonstrates that certain defatted bone particulate/polyurethane materials show improved mechanical properties (e.g., compressive modulus and strength). In some embodiments, provided composites show wet compressive modulus that is at least 1.5 times higher than that observed with otherwise comparable composites with protected bone particulates. In some embodiments, provided composites show wet compressive modulus that is at least 2.5 times higher than that observed with otherwise comparable composites with protected bone particulates.

It is well appreciated in the art that allograft bone has adequate weight-bearing mechanical properties and can remodel from the external surface to the interior (Khan S N, Cammisa F P, Sandbu H S, Diwan A D, Girardi F P, Lane J M. The biology of bone grafting. Journal of the American Academy of Orthopaedic Surgeons 2005; 13:77). The present invention, among other things, discloses that certain composites and/or compositions wherein the particular material has an average particle size of 105-500 µm. Without wishing to be bound by any particular theory, the present invention encompasses the recognition that defatted bone particles with an average particle size of 105-500 µm may facilitates remodeling through the process of creeping substitution (T I Malinin, E M Carpenter, and H T Temple. Particulate Bone Allograft Incorporation in Regeneration of Osseous Defects; Importance of Particle Sizes. The Open Orthopaedics Journal, 2007, 1, 19-24). The present invention also discloses that certain composites and/or compositions demonstrating good loading-bearing properties, wherein the particular material is about 50-60 vol % or 54-58 vol % of the composites and/or compositions. In some embodiments, the present invention provides composites and/or compositions comprising a polyurethane material and defatted bone particulates, wherein the defatted bone particulates have an average particle size of 105-500 µm and are about 50-60 vol % of the composites and/or compositions, provides surprising and beneficial attributes. In some embodiments, provided composites and/or compositions comprise a polyurethane material and defatted bone particulates, wherein provided composites and/or compositions after being fully hardened have a porosity less than 10%, 5%, 3%, or 2%. In some embodiments, provided composites and/or compositions comprise a polyurethane material and defatted bone particulates, wherein provided composites and/or compositions remodel by 50% within 1, 2, or 3 months. Without being bound by any particular theory, the above composites and/or compositions provides balance between mechanical and remodeling.

In some embodiments, the present invention provides composites and/or compositions comprising a particulate material and a polyurethane material wherein the particulate material does not comprise defatted bone particles. In general, the present invention provides composites and/or compositions comprising a treated (e.g., surface-modified) particulate material. In some embodiments, provided composites and/or compositions comprise bone particles containing modifications other than those achieved through defatting (e.g., in some embodiments, demineralization, in particular, surface demineralization). In some embodiments, provided composites and/or compositions comprise treated particulates that are not bone, such as an inorganic material (e.g., tricalcium phosphate), a bone substitute material, a composite material, or any combinations thereof.

In many embodiments, the present invention demonstrates that composites containing bone particles show beneficial attributes as compared with non-bone particles. However, according to the present invention and as described herein, the present invention establishes many benefits of, an provides compositions and methods relating to, certain composites and/or compositions that comprise non-bone particulate materials and polyurethane materials.

Other aspects, features and advantages will be apparent from the description of the following embodiments and from the claims.

DEFINITIONS

The term "bioactive agent" is used herein to refer to compounds or entities that alter, promote, speed, prolong, inhibit, activate, or otherwise affect biological or chemical events in a subject (e.g., a human). For example, bioactive agents may include, but are not limited to osteogenic, osteoinductive, and osteoconductive agents, anti-HIV substances, anti-cancer substances, antibiotics, immunosuppressants, anti-viral agents, enzyme inhibitors, neurotoxins, opioids, hypnotics, anti-histamines, lubricants, tranquilizers, anti-convulsants, muscle relaxants, anti-Parkinson agents, anti-spasmodics and muscle contractants including channel blockers, miotics and anti-cholinergics, anti-glaucoma compounds, anti-parasite agents, anti-protozoal agents, and/or anti-fungal agents, modulators of cell-extracellular matrix interactions including cell growth inhibitors and anti-adhesion molecules, vasodilating agents, inhibitors of DNA, RNA, or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotics, targeting agents, chemotactic factors, receptors, neurotransmitters, proteins, cell response modifiers, cells, peptides, polynucleotides, viruses, and vaccines. In certain embodiments, the bioactive agent is a drug. In certain embodiments, the bioactive agent is a small molecule.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, the United States Pharmacopeia-25/National Formulary-20, published by the United States Pharmcopeial Convention, Inc., Rockville Md., 2001, and the "Pharmazeutische Wirkstoffe", edited by Von Keemann et al., Stuttgart/New York, 1987, all of which are incorporated herein by reference. Drugs for human use listed by the U.S. Food and Drug Administration (FDA) under 21 C.F.R. § § 330.5, 331 through 361, and 440 through 460, and drugs for veterinary use listed by the FDA under 21 C.F.R. § § 500 through 589, all of which are incorporated herein by reference, are also considered acceptable for use in accordance with the present invention.

The terms, "biodegradable", "bioerodable", or "resorbable" materials, as used herein, are intended to describe materials that degrade under physiological conditions to form a product that can be metabolized or excreted without damage to the subject. In certain embodiments, the product is metabolized or excreted without permanent damage to the subject. Biodegradable materials may be hydrolytically degradable, may require cellular and/or enzymatic action to fully degrade, or both. Biodegradable materials also include materials that are broken down within cells. Degradation may occur by hydrolysis, oxidation, enzymatic processes, phagocytosis, or other processes.

The term "biocompatible" as used herein, is intended to describe materials that, upon administration in vivo, do not induce undesirable side effects. In some embodiments, the material does not induce irreversible, undesirable side effects. In certain embodiments, a material is biocompatible if it does not induce long term undesirable side effects. In certain embodiments, the risks and benefits of administering a material are weighed in order to determine whether a material is sufficiently biocompatible to be administered to a subject.

The term "biomolecules" as used herein, refers to classes of molecules (e.g., proteins, amino acids, peptides, polynucleotides, nucleotides, carbohydrates, sugars, lipids, nucleoproteins, glycoproteins, lipoproteins, steroids, natural products, etc.) that are commonly found or produced in cells, whether the molecules themselves are naturally-occurring or artificially created (e.g., by synthetic or recombinant methods). For example, biomolecules include, but are not limited to, enzymes, receptors, glycosaminoglycans, neurotransmitters, hormones, cytokines, cell response modifiers such as growth factors and chemotactic factors, antibodies, vaccines, haptens, toxins, interferons, ribozymes, anti-sense agents, plasmids, DNA, and RNA. Exemplary growth factors include but are not limited to bone morphogenic proteins (BMP's) and their active fragments or subunits. In some embodiments, the biomolecule is a growth factor, chemotactic factor, cytokine, extracellular matrix molecule, or a fragment or derivative thereof, for example, a cell attachment sequence such as a peptide containing the sequence, RGD.

The term "composite" as used herein, is used to refer to a unified combination of two or more distinct materials. A composite may be homogeneous or heterogeneous. For example, a composite may be a combination of particles and a polymer; or a combination of particles, polymers and antibiotics. In certain embodiments, a composite has a particular orientation. The term "composition" as used herein, is used to refer to any combination of two or more distinct materials. A composite can refer to a composition with substantially uniform composition and/or characteristics.

The term "defatted" is used herein applied to particles (e.g., bone particles), refers to particles that have been subjected to a process for reduction of fat content. In some embodiments, to obtain defatted bone particles (DFMBP), mineralized bone particles were stirred with a 50/50% volume solution of acetone/chloroform in a volumetric ratio of 1:15 for 4 days. The defatted bone was then washed with acetone and lyophilized for at least 48 h.

The term "demineralized" is used herein to refer to particles (e.g., bone particles) that have been subjected to a process that causes a decrease in the original mineral content. As utilized herein, the phrase "superficially demineralized" as applied to bone particles refers to bone particles possessing at least about 90% by weight of their original inorganic mineral content. The phrase "partially demineralized" as applied to the bone particles refers to bone particles possessing from about 8% to about 90% by weight of their original inorganic mineral content, and the phrase "fully demineralized" as applied to the bone particles refers to bone particles possessing less than about 8% by weight, for example, less than about 1% by weight, of their original inorganic mineral content. The unmodified term "demineralized" as applied to the bone particles is intended to cover any one or combination of the foregoing types of demineralized bone particles.

The term "deorganified" as herein applied to matrices, particles, etc., refers to bone or cartilage matrices, particles, etc., that were subjected to a process that removes at least part of their original organic content. In some embodiments, at least 1%, 10%, 20%, 30%, 40%, 50%, 60%, 70%, 80%, 90%, or 99% of the organic content of the starting material is removed. Deorganified bone from which substantially all the organic components have been removed is termed "anorganic."

The term "flowable polymer material" as used herein, refers to a flowable composition including one or more of monomers, pre-polymers, oligomers, low molecular weight polymers, uncross-linked polymers, partially cross-linked polymers, partially polymerized polymers, polymers, or combinations thereof that have been rendered formable. One skilled in the art will recognize that a flowable polymer material need not be a polymer but may be polymerizable. In some embodiments, flowable polymer materials include polymers that have been heated past their glass transition or melting point. Alternatively or in addition, a flowable polymer material may include partially polymerized polymer, telechelic polymer, or prepolymer. A pre-polymer is a low molecular weight oligomer typically produced through step growth polymerization. The pre-polymer is formed with an excess of one of the components to produce molecules that are all terminated with the same group. For example, a diol and an excess of a diisocyanate may be polymerized to produce isocyanate terminated prepolymer that may be combined with a diol to form a polyurethane. Alternatively or in addition, a flowable polymer material may be a polymer material/solvent mixture that sets when the solvent is removed.

The term "flowable state" as used herein, refers to a state when a composition, under appropriate conditions, may have flow characteristics that range from thick, flowable liquids to moldable, dough-like substances. In some embodiments, a composition has a low enough viscosity to be suitable for injection. In come embodiments, a composition is workable so that it can be molded into an implantation site. Once cured (e.g., set and/or hardened), a composition may result in a composite including particles (e.g., bone particles and/or particulate inorganic materials such as CaP) and polymer (e.g., polyurethane materials). In some embodiments, a composition may include particles and a reactive liquid of polyurethane. Such a reactive liquid can be a two-component composition for polyurethane include at least a polyisocyanate, a polyol, and a catalyst, and optionally additional components such as water, a stabilizer, a porogen, a plasticizer, a chain extender, a wetting agent, etc. In some embodiments, a composition may include bioactive agents to be delivered such as antibiotics, growth factors, etc. Viscosity or consistency of a composition may change from when it is initially prepared (e.g., in a flowable state). For example, a composition can initially have a flowable, liquid-like consistency, which allows it to be easily injected and applied to certain surfaces such as on a prosthesis or a bone. Flowable consistency also allows a composition (e.g., a flowable cement) to penetrate trabeculae of bone. Over the course that a composite material is handled (e.g., 2-5 minutes), it can become more viscous (e.g., dough-like), which allows it to act as a grout (e.g., to fill gaps, holes, and defects) and to be moldable by hand. Increase in viscosity can also provide a composition mechanical strength to fix and to stabilize a prosthesis until a hardened composite is resorbed and/or remodeling or in-growth occurs (e.g., over approximately 0.2, 0.3, 0.5, 1 or 2 years). In some embodiments, after a composition is applied, it can harden substantially to serve as a load-bearing composite material. A hardened composition (e.g., a composite) is not moldable by hand and not noticeably affected by heat or irrigation.

The term "non-demineralized" as herein applied to bone or bone particles, refers to bone or bone-derived material (e.g., particles) that have not been subjected to a demineralization process (i.e., a procedure that totally or partially removes the original inorganic content of bone).

The term "nontoxic" is used herein to refer to substances which, upon ingestion, inhalation, or absorption through the skin by a human or animal, do not cause, either acutely or chronically, damage to living tissue, impairment of the central nervous system, severe illness or death.

The term "osteoconductive" as used herein, refers to the ability of a substance or material to provide surfaces which are receptive to the growth of new bone.

The term "osteogenic" as used herein, refers to the ability of a substance or material that can induce bone formation.

The term "osteoinductive" as used herein, refers to the quality of being able to recruit cells (e.g., osteoblasts) from the host that have the potential to stimulate new bone formation. In general, osteoinductive materials are capable of inducing heterotopic ossification, that is, bone formation in extraskeletal soft tissues (e.g., muscle).

The term "osteoimplant" is used herein in its broadest sense and is not intended to be limited to any particular shapes, sizes, configurations, compositions, or applications. Osteoimplant refers to any device or material for implantation that aids or augments bone formation or healing. Osteoimplants are often applied at a bone defect site, e.g., one resulting from injury, defect brought about during the course of surgery, infection, malignancy, inflammation, or developmental malformation. Osteoimplants can be used in a variety of orthopedic, neurosurgical, dental, and oral and maxillofacial surgical procedures such as the repair of simple and compound fractures and non-unions, external, and internal fixations, joint reconstructions such as arthrodesis, general arthroplasty, deficit filling, disectomy, laminectomy, anterior cerival and thoracic operations, spinal fusions, etc.

The term "polyurethane" and "PUR" as used herein, is intended to include all polymers incorporating more than one urethane group (—NH—CO—O—) in the polymer backbone. Polyurethane materials, in some embodiments, refer to the compositions formed by the reaction of a polyisocyanate (such as a diisocyanate) and a polyol (such as a diol), optionally with any additional components. For example,

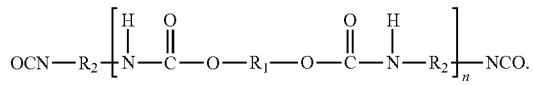

In some embodiments, polyurethane materials refer to the compositions comprising a polyisocyanate (such as a diisocyanate) and a polyol (such as a diol), and optionally a catalyst.

The term "porogen" as used herein, refers to a chemical compound that may be part of a composite material and upon implantation/injection or prior to implantation/injection diffuses, dissolves, and/or degrades to leave a pore in the osteoimplant composite. A porogen may be introduced into a composite material during manufacture, during preparation of composite materials (e.g., in the operating room), or after implantation, delivery and/or injection of composite materials. A porogen essentially reserves space in a composite material while the composite material is being molded but once the composite is implanted the porogen diffuses, dissolves, or degrades, thereby inducing porosity into composite materials. In this way porogens provide latent pores.

In certain embodiments, a porogen may be leached out of the composite before implantation, delivery and/or injection. This resulting porosity of the implant generated during manufacture or after implantation, delivery and/or injection (i.e., "latent porosity") is thought to allow infiltration by cells, bone formation, bone remodeling, osteoinduction, osteoconduction, and/or faster degradation of the osteoimplant. A porogen may be a gas (e.g., carbon dioxide, nitrogen, or other inert gas), liquid (e.g., water, biological fluid), or solid. Porogens are typically water soluble such as salts, sugars (e.g., sugar alcohols), polysaccharides (e.g., dextran (poly(dextrose)), water soluble small molecules, etc. Porogens can also be natural or synthetic polymers, oligomers, or monomers that are water soluble or degrade quickly under physiological conditions. Exemplary polymers include polyethylene glycol, poly(vinylpyrollidone), pullulan, poly(glycolide), poly(lactide), poly(lactide-co-glycolide), other polyesters, and starches. In certain embodiments, bone particles utilized in composite materials or compositions act as porogens. For example, osteoclasts resorb allograft and make pores in composite materials. In some embodiments, porogens may refer to a blowing agent (i.e., an agent that participates in a chemical reaction to generate a gas). Water may act as such a blowing agent or porogen.

The term "porosity" as used herein, refers to the average amount of non-solid space contained in a composite. Such space is considered void of volume even if it contains a substance that is liquid at ambient or physiological temperature, e.g., 0.5° C. to 50° C. Porosity or void volume of a composite can be defined as the ratio of the total volume of the pores (i.e., void volume) in the material to the overall volume of composite materials. In some embodiments, porosity (ε), defined as the volume fraction pores, can be calculated from composite foam density, which can be measured gravimetrically. Porosity may in certain embodiments refer to "latent porosity" wherein pores are only formed upon diffusion, dissolution, or degradation of a material occupying the pores. In such an instance, pores may be formed after implantation, delivery and/or injection. It will be appreciated by these of ordinary skill in the art that porosity of a composite or a composition may change over time, in some embodiments, after implantation, delivery and/or injection (e.g., after leaching of a porogen, when osteoclasts resorbing allograft bone, etc.). For the purpose of the present disclosure, the beginning of mixing of components of such composite materials utilized in the present invention may be considered to be "time zero" ($T_0$). In some embodiments, a composition (e.g., a composite) has a porosity of as low as 1 vol % or 2 vol % at time zero. In some embodiments, a composition cures before implantation and have a porosity of less than 2 vol %, less than 5 vol %, less than 10 vol %, less than 15 vol %, less than 20 vol %, less than 30 vol %, less than 40 vol %, or less than 50 vol %, after being hardened fully. In some embodiments, a composition cures in situ and have a porosity of less than 2 vol %, less than 5 vol %, less than 10 vol %, less than 15 vol %, less than 20 vol %, less than 30 vol %, less than 40 vol %, or less than 50 vol % after being hardened fully. At the end of hardening of such a composition (e.g., a composite), when its viscosity reaches a certain value and levels off (e.g., when components of the composite complete polymerization) may be considered to be "time end" ($T_h$).

The term "remodeling" as used herein, describes the process by which native bone, processed bone allograft, whole bone sections employed as grafts, and/or other bony tissues are replaced with new cell-containing host bone tissue by the action of osteoclasts and osteoblasts. Remodeling also describes the process by which non-bony native tissue and tissue grafts (e.g., bone and/or non-bone particles) are removed and replaced with new, cell-containing tissue in vivo. Remodeling also describes how inorganic materials (e.g., calcium-phosphate materials, such as β-tricalcium phosphate) is replaced with living bone. A remodeling process may continue for weeks, months, or years. In some embodiments, particulate materials used in accordance with the present invention may be remodeled by 50% within about 4-6 weeks, 6-8 weeks, 8-12 weeks, 12-24 weeks, 2-6 months, or 6-12 months. In some embodiments, particulate materials used in accordance with the present invention may be remodeled by 50% within about 1-3 months.

The term "setting time" as used herein, is approximated by the tack-free time (TFT), which is defined as the time at which a material could be touched with a spatula with no adhesion of the spatula to the foam of the material. At the TFT, wound could be closed without altering properties of a material. The terms "set" and "harden" as used herein may be interchangeable.

The term "shaped" as used herein, is intended to characterize a material (e.g., composite material) or an osteoimplant refers to a material or osteoimplant of a determined or regular form or configuration in contrast to an indeterminate or vague form or configuration (as in the case of a lump or other solid matrix of special form). Materials may be shaped into any shape, configuration, or size. For example, materials can be shaped as sheets, blocks, plates, disks, cones, pins, screws, tubes, teeth, bones, portions of bones, wedges, cylinders, threaded cylinders, and the like, as well as more complex geometric configurations.

The term "transformation" as used herein, describes a process by which a material is removed from an implant site and replaced by host tissue after implantation. Transformation may be accomplished by a combination of processes, including but not limited to remodeling, degradation, resorption, and tissue growth and/or formation. Removal of the material may be cell-mediated or accomplished through chemical processes, such as dissolution and hydrolysis.

The term "wet compressive strength" as used herein, refers to the compressive strength of an osteoimplant after being immersed in physiological saline (e.g., phosphate-buffered saline (PBS), water containing 0.9 g NaCl/100 ml water, etc.) for a minimum of 12 hours (e.g., 24 hours). Compressive strength and modulus are well-known measurements of mechanical properties and is measured using the procedure described herein.

The term "working time" as used herein, is defined in the ISO9917 standard as "the period of time, measured from the start of mixing, during which it is possible to manipulate a dental material without an adverse effect on its properties" (Clarkin et al.,*J Mater Sci: Mater Med* 2009; 20:1563-1570). In some embodiments, the working time for a two-component polyurethane is determined by the gel point, the time at which the crosslink density of the polymer network is sufficiently high that the material gels and no longer flows. According to the present invention, the working time is measured by loading the syringe with the reactive composite material and injecting <0.25 ml every 30 s. The working time is noted as the time at which the material was more difficult to inject, indicating a significant change in viscosity.

The term "load-bearing" as used herein, refers to the ability of a material to bear weight and force resting upon it, conducting a vertical load from the upper structure to the foundation. Measurements of stiffness may be used as a promising tool for indicating load-bearing capacity. In this context, compressive strength may be referred to characterize the load-bearing capacity of a material (e.g., a hardened composition/composite). For example, a material having wet compressive strength of 0.1 MPa or more than 0.1 MPa is considered load-bearing, while having wet compressive strength of less than 0.1 MPa is non-load-bearing. In some embodiments, a material having wet compressive strength of more than 0.5 MPa, 1 MPa, or 3 MPa is load-bearing. Correspondingly, a material having wet compressive strength of less than 0.5 MPa, 1 MPa, or 3 MPa is non-load-bearing in some embodiments. In some embodiments, a composite/composition utilized in accordance with the present invention are load-bearing. In certain embodiments, they are non-load-bearing.

DETAILED DESCRIPTION OF CERTAIN EMBODIMENTS

Figure 1:
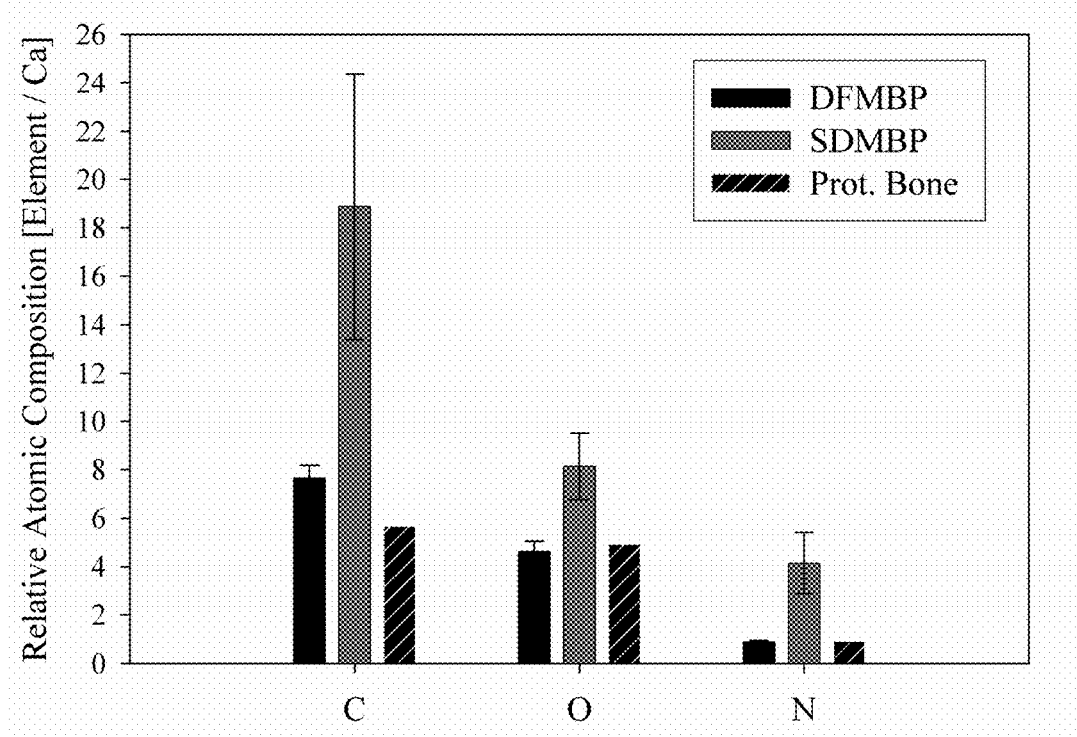
FIG. 1 XPS analysis. Relative atomic compositions of the surface of DFMBP, SDMBP, and Prot. Bone FIG. 2*a*. Thermogravimetrical analysis of DFMBP/PUR composites.

As used herein and in the appended claims, the singular forms "a," "an" and "the" include plural references unless the content clearly dictates otherwise. All publications, patent applications, patents, and other references mentioned herein are incorporated by reference in their entirety.

Particulates/polyurethane compositions (e.g., a composite) described herein include particulates (e.g., bone particles and ceramic biomaterials such as calcium phosphate), polyurethane, and in some embodiments, one or more additional components (e.g., a porogen and/or a bioactive agent). As described below, particulates and biodegradable polyurethanes are combined to form a porous composite (e.g., an osteoimplant). Particulates can be treated (e.g., surface modified) to adjust their reactivity to polymer matrix. In some embodiments, particulates are treated to increase surface reactivity in order to improve interfacial binding with PUR matrix (e.g., via reaction towards isocyanates polymers). and thus resulting in enhanced mechanical properties. In some embodiments, porous composites retain strength and are replaced by new tissue when present in a body. In some embodiments, composites degrade and remodel.

Inventive composites can be used in a large variety of clinical applications, for example, as bone void fillers, to repair or help healing of skeletal deficiencies resulting from trauma, tumors, surgery, iatrogenic, congenital, genetic, metabolic and degenerative or abnormal development, and inflammatory infection. In some embodiments, inventive composites promote cellular infiltration from adjacent osseous tissues, thus accelerating the remodeling process.

The invention also provides methods of preparing and using inventive composites as well as kits for preparing and/or administering inventive composites. Inventive porous composites may be prepared using any of a variety of methods. In some embodiments, inventive composites are prepared using a method that includes a catalyst (e.g., a stannous octoate catalyst). In some embodiments, bone particles and/or other bone substitute materials are combined with polyurethanes and injected, extruded, molded, or similarly delivered to a tissue site (e.g., bony defect) of a subject. Inventive composites are engineered to set in situ to form a solid composite that may have a desired or predetermined mechanical strength. In certain embodiments, polyurethane present in a composition or composite may include monomers or pre-polymers. In some embodiments, polyurethane is a polymer that has been rendered formable through combination of two liquid components (i.e., a polyisocyanate prepolymer and a polyol).

Particulate Component

Particles used in accordance with the present invention may include a bone-derived material, an inorganic material, a bone substitute material, a composite material, or any combinations thereof.

Bone Particles

Any kind of bone and/or bone-derived particles may be used in the present invention. In some embodiments, bone particles employed in the preparation of bone particle-containing composites are obtained from cortical, cancellous, and/or corticocancellous bone. Bone particles may be obtained from any vertebrate. Bone may be of autogenous, allogenic, and/or xenogeneic origin. In certain embodiments, bone particles are autogenous, that is, bone particles are from the subject being treated. In other embodiments, bone particles are allogenic (e.g., from donors). In certain embodiments, the source of bone may be matched to the eventual recipient of inventive composites (i.e., the donor and recipient are of the same species). For example, human bone particle is typically used in a human subject. In certain embodiments, bone particles are obtained from cortical bone of allogenic origin. In certain embodiments, bone particles are obtained from bone of xenogeneic origin. Porcine and bovine bone are types of xenogeneic bone tissue that can be used individually or in combination as sources for bone particles and may offer advantageous properties. Xenogenic bone tissue may be combined with allogenic or autogenous bone.

Bone particles can be formed by any process known to break down bone into small pieces. Exemplary processes for forming such particles include milling whole bone to produce fibers, chipping whole bone, cutting whole bone, grinding whole bone, fracturing whole bone in liquid nitrogen, or otherwise disintegrating the bone. Bone particles can optionally be sieved to produce particles of a specific size range. Bone particles may be of any shape or size. Exemplary shapes include spheroidal, plates, shards, fibers, cuboidal, sheets, rods, oval, strings, elongated particles, wedges, discs, rectangular, polyhedral, etc.

In some embodiments, bone particles have an average size (e.g., medium or mean dimensions) about 1200 microns, 1100 microns, 1000 microns, 900 microns, 800 microns, 700 microns, 600 microns, 500 microns, 400 microns, 300 microns, 200 microns, 100 microns, etc. In some embodiments, diameters of bone particles are within a range between any of such sizes. For example, medium or mean diameters of bone particles have a range from approximately 100 microns to approximately 1000 microns. In some embodiments, bone particles have an average size (e.g., medium or mean dimensions) in a range of 105-500 microns.

As for irregularly shaped bone particles, recited dimension ranges may represent the length of the greatest or smallest dimension of the particle. As examples, bone particles can be pin shaped, with tapered ends having an average diameter of from about 100 microns to about 500 microns. As will be appreciated by one of skill in the art, for injectable compositions, the maximum particle size will depend in part on the size of the cannula or needle through which the material will be delivered.

In some embodiments, particle size distribution of bone particles utilized in accordance with the present inventions with respect to a mean value or a median value may be plus or minus, e.g., about 10% or less of the mean value, about 20% or less of the mean value, about 30% or less of the mean value, about 40% or less of the mean value, about 50% or less of the mean value, about 60% or less of the mean value, about 70% or less of the mean value, about 80% or less of the mean value, or about 90% or less of the mean value.

For bone particles that are fibers or other elongated particles, in some embodiments, at least about 90 percent of the particles possess a median or mean length in their greatest dimension in a range from approximately 100 microns to approximately 1000 microns. Particles may possess a median or mean length to median or mean thickness ratio from at least about 5:1 up to about 500:1, for example, from at least about 50:1 up to about 500:1, or from about 50:1 up to about 100:1; and a median or mean length to median or mean width ratio of from about 10:1 to about 200:1 and, for example, from about 50:1 to about 100:1. In certain embodiments, bone particles are short fibers having a cross-section of about 300 microns to about 100 microns and a length of about 0.1 mm to about 1 mm.

Processing of bone to provide particles may be adjusted to optimize for the desired size and/or distribution of bone particles. The properties of resulting inventive composites (e.g., mechanical properties) may also be engineered by adjusting weight percent, shapes, sizes, distribution, etc. of bone particles or other particles. For example, an inventive composite may be made more viscous and load bearing by including a higher percentage of particles.

U.S. Pat. Nos. 5,899,939; 5,507,813; 6,123,731; 6,294,041; 6,294,187; 6,332,779; 6,440,444; and 6,478,825; the contents of all of which are incorporated herein by reference, describe methods for preparing composites including allogenic bone for use in orthopedic applications.

Bone Treatment

Bone particles utilized in accordance with the present invention can be treated to enhance their interaction with polyurethanes and/or to confer some properties to particle surface. While some bone particles will interact readily with monomers and be covalently linked to polyurethane materials, it may be desirable to modify surface of bone particles to facilitate their incorporation into polymers. Modification (e.g., surface modification) may provide a chemical substance that is strongly bonded to the surface of bone, e.g., covalently bonded to the surface. Bone particles may, alternatively or additionally, be coated with a material to facilitate interaction with polymers of inventive composites.

Bone particles utilized in accordance with the present inventions may be demineralized, non-demineralized, mineralized, or anorganic. In some embodiments, at least some bone particles are used "as is" in preparing inventive composites. In some embodiments, at least some bone particles are defatted and disinfected. Aqueous solutions can be used. Organic solvent may also be used in the defatting and disinfecting bone particles. For example, methanol, ethanol, isopropanol, butanol, DMF, DMSO, acetone, diethyl ether, hexanes, glyme, tetrahydrofuran, chloroform, methylene chloride, and carbon tetrachloride may be used. An exemplary defatting/disinfectant solution is a 50%/50% volume solution of acetone/chloroform. In certain embodiments, a non-halogenated solvent is used. A defatting/disinfectant solution may also include a detergent (e.g., an aqueous solution of a detergent). Ordinarily, at least about 10 to about 40 percent by weight of water (i.e., about 60 to about 90 weight percent of defatting agent such as alcohol) should be present in the defatting/disinfecting solution to produce optimal lipid removal and disinfection within the shortest period of time. An exemplary concentration range of a defatting solution is from about 60 to about 85 weight percent alcohol, for example, about 70 weight percent alcohol.

In some embodiments, at least some bone particles are demineralized. Bone particles can be optionally demineralized in accordance with known and/or conventional procedures in order to reduce their inorganic mineral content. Demineralization methods remove the inorganic mineral component of bone by employing acid solutions. Such methods are well known in the art, see for example, Reddi, et al., *Proc. Nat. Acad. Sci.*, 1972, 69:1601-1605, the contents of which are incorporated herein by reference. The strength of the acid solution, the shape and dimensions of the bone particles and the duration of the demineralization treatment will determine the extent of demineralization. Reference in this regard is made to Lewandrowski, et al., *J. Biomed. Mater. Res.*, 1996, 31:365-372 and U.S. Pat. No. 5,290,558, the contents of both of which are incorporated herein by reference.

In an exemplary defatting/disinfecting/demineralization procedure, bone particles are subjected to a defatting/disinfecting step, followed by an acid demineralization step. Following defatting, bone particles can be immersed in acid over time to effect their demineralization. The acid also disinfects the bone by killing viruses, vegetative microorganisms, and spores. Acids which can be employed in this step include inorganic acids such as hydrochloric acid and organic acids such as peracetic acid. After acid treatment, demineralized bone particles can be rinsed with sterile water to remove residual amounts of acid and thereby raise the pH. Bone particles may be dried, for example, by lyophilization, before being incorporated into a composite. Bone particles may be stored under aseptic conditions, for example, in a lyophilized state, until they are used or sterilized using known methods (e.g., gamma irradiation) shortly before combining them with polyurethane materials used in inventive compositions (e.g., composites).

As utilized herein, the phrase "superficially demineralized" as applied to the bone particles refers to bone particles possessing at least about 90% by weight of their original inorganic mineral content. The phrase "partially demineralized" as applied to the bone particles refers to bone particles possessing from about 8% to about 90% weight of their original inorganic mineral content, and the phrase "fully demineralized" as applied to the bone particles refers to bone particles possessing less than about 8%, preferably less than about 1%, by weight of their original inorganic mineral content. The unmodified term "demineralized" as applied to the bone particles is intended to cover any one or combination of the foregoing types of demineralized bone particles, that is, superficially demineralized, partially demineralized, or fully demineralized bone particles.

In alternative embodiments, surfaces of bone particles may be lightly demineralized according to the procedures in our commonly owned U.S. Patent Application, U.S. Ser. No. 10/285,715, filed Nov. 1, 2002, published as U.S. Patent Publication No. 2003/0144743, on Jul. 31, 2003, the contents of which are incorporated herein by reference. Even minimal demineralization, for example, of less than 5% removal of the inorganic phase, increases the hydroxylation of bone fibers and the surface concentration of amine groups. Demineralization may be so minimal, for example, less than 1%, that the removal of the calcium phosphate phase is almost undetectable. Rather, the enhanced surface concentration of reactive groups defines the extent of demineralization. This may be measured, for example, by titrating the reactive groups. Surface composition can also be measured by x-ray photoelectron spectroscopy (XPS), an experimental technique that measures the atomic composition of the top 1-10 nm of the surface. In some embodiments, in a polymerization reaction that utilizes the exposed allograft surfaces to initiate a reaction, the amount of unreacted monomer remaining may be used to estimate reactivity of the surfaces. Surface reactivity may be assessed by a surrogate mechanical test, such as a peel test of a treated coupon of bone adhering to a polymer.

In certain embodiments, bone particles are subjected to a process that partially or totally removes their initial organic content to yield mineralized and anorganic bone particles, respectively. Different mineralization methods have been developed and are known in the are (Hurley, et al., *Milit. Med.* 1957, 101-104; Kershaw, *Pharm. J.* 6:537, 1963; and U.S. Pat. No. 4,882,149; each of which is incorporated herein by reference). For example, a mineralization procedure can include a de-greasing step followed by a basic treatment (with ammonia or another amine) to degrade residual proteins and a water washing (U.S. Pat. Nos. 5,417,975 and 5,573,771; both of which are incorporated herein by reference). Another example of a mineralization procedure includes a defatting step where bone particles are sonicated in 70% ethanol for 1-3 hours.

In some embodiments, bone particles can be modified in one or more ways, e.g., their protein content can be augmented or modified as described, for example, in U.S. Pat. Nos. 4,743,259 and 4,902,296, the contents of both of which are incorporated herein by reference.

Mixtures or combinations of one or more of the foregoing types of bone particles can be employed. For example, one or more of the foregoing types of demineralized bone particles can be employed in combination with non-demineralized bone particles, i.e., bone particles that have not been subjected to a demineralization process, or inorganic materials. The amount of each individual type of bone particle employed can vary widely depending on the mechanical and biological properties desired. Thus, in some embodiments, mixtures of bone particles of various shapes, sizes, and/or degrees of demineralization may be assembled based on the desired mechanical, thermal, chemical, and biological properties of a composite. A desired balance between the various properties of composites (e.g., a balance between mechanical and biological properties) may be achieved by using different combinations of particles. Suitable amounts of various particle types can be readily determined by those skilled in the art on a case-by-case basis by routine experimentation.

The differential in strength, osteogenicity, and other properties between partially and fully demineralized bone particles on the one hand, and non-demineralized, superficially demineralized bone particles, inorganic ceramics, and other bone substitutes on the other hand can be exploited. For example, in order to increase the compressive strength of an osteoimplant, the ratio of nondemineralized and/or superficially demineralized bone particles to partially or fully demineralized bone particles may favor the former, and vice versa. Bone particles in composites also play a biological role. Non-demineralized bone particles bring about new bone in-growth by osteoconduction. Demineralized bone particles likewise play a biological role in bringing about new bone in-growth by osteoinduction. Both types of bone particles are gradually remodeled and replaced by new host bone as degradation of the composite progresses over time. Thus, the use of various types of bone particles can be used to control the overall mechanical and biological properties, (e.g., strength, osteoconductivity, and/or osteoinductivity, etc.) of osteoimplants.

In some embodiments, bone particle surface is chemically treated before being mixed with polyurethane. For example, non-demineralized bone particles may be rinsed with phosphoric acid, e.g., for 1 to 15 minutes in a 5-50% solution by volume. Those skilled in the art will recognize that the relative volume of bone particles and phosphoric acid solution (or any other solution used to treat bone particles), may be optimized depending on the desired level of surface treatment. Agitation will also increase the uniformity of the treatment both along individual particles and across an entire sample of particles. A phosphoric acid solution reacts with mineral components of bone particles to coat the bone particles with calcium phosphate, which may increase the affinity of the surface for inorganic coupling agents such as silanes and for polymer components of the composite. As noted above, bone particle surface may be partially demineralized to expose the collagen fibers.

Collagen fibers exposed by demineralization are typically relatively inert but have some exposed amino acid residues that can participate in reactions. Collagen may be rendered more reactive by fraying triple helical structures of the collagen to increase exposed surface area and number of exposed amino acid residues. This not only increases surface area of bone particles available for chemical reactions but also for their mechanical interactions with polymers as well. Rinsing partially demineralized bone particles in an alkaline solution will fray collagen fibrils. For example, bone particles may be suspended in water at a pH of about 10 for about 8 hours, after which the solution is neutralized. One skilled in the art will recognize that this time period may be increased or decreased to adjust the extent of fraying. Agitation, for example, in an ultrasonic bath, may reduce the processing time. Alternatively or additionally, bone particles may be sonicated with water, surfactant, alcohol, or some combination of these.

In some embodiments, collagen fibers at bone particle surface may be cross-linked. A variety of cross-linking techniques suitable for medical applications are well known in the art (see, for example, U.S. Pat. No. 6,123,781, the contents of which are incorporated herein by reference). For example, compounds like 1-ethyl-3-(3-dimethylaminopropyl)carbodiimide hydrochloride, either alone or in combination with N-hydroxysuccinimide (NHS) will crosslink collagen at physiologic or slightly acidic pH (e.g., in pH 5.4 MES buffer). Acyl azides and genipin, a naturally occurring bicyclic compound including both carboxylate and hydroxyl groups, may also be used to cross-link collagen chains (see Simmons, et al, *Biotechnol. Appl. Biochem.,* 1993, 17:23-29; PCT Publication WO98/19718, the contents of both of which are incorporated herein by reference). Alternatively or additionally, hydroxymethyl phosphine groups on collagen may be reacted with the primary and secondary amines on neighboring chains (see U.S. Pat. No. 5,948,386, the entire contents of which are incorporated herein by reference). Standard cross-linking agents such as mono- and dialdehydes, polyepoxy compounds, tanning agents including polyvalent metallic oxides, organic tannins, and other plant derived phenolic oxides, chemicals for esterification or carboxyl groups followed by reaction with hydrazide to form activated acyl azide groups, dicyclohexyl carbodiimide and its derivatives and other heterobifunctional crosslinking agents, hexamethylene diisocyanate, and sugars may also be used to cross-link collagens. Bone particles are then washed to remove all leachable traces of materials. In other embodiments, enzymatic cross-linking agents may be used. Additional cross-linking methods include chemical reaction, irradiation, application of heat, dehydrothermal treatment, enzymatic treatment, etc. One skilled in the art will easily be able to determine the optimal concentrations of cross-linking agents and incubation times for the desired degree of cross-linking.

Both frayed and unfrayed collagen fibers may be derivatized with monomer, pre-polymer, oligomer, polymer, initiator, and/or biologically active or inactive compounds, including but not limited to biomolecules, bioactive agents, small molecules, inorganic materials, minerals, through reactive amino acids on the collagen fiber such as lysine, arginine, hydroxylysine, proline, and hydroxyproline. Monomers that link via step polymerization may react with these amino acids via the same reactions through which they polymerize. Vinyl monomers and other monomers that polymerize by chain polymerization may react with these amino acids via their reactive pendant groups, leaving the vinyl group free to polymerize. Alternatively, or in addition, bone particles may be treated to induce calcium phosphate deposition and crystal formation on exposed collagen fibers. Calcium ions may be chelated by chemical moieties of the collagen fibers, and/or calcium ions may bind to the surface of the collagen fibers. James et al., *Biomaterials* 20:2203-2313, 1999; incorporated herein by reference. The calcium ions bound to the collagen provides a biocompatible surface, which allows for the attachment of cells as well as crystal growth. The polymer will interact with these fibers, increasing interfacial area and improving the wet strength of the composite.

Non-bone Particulates

Alternatively or additionally, any type of particulates comprising inorganic materials and/or other bone substitute materials (i.e., compositions similar to natural bone such as collagen, biocompatible polymers, osteoinductive agents, other commercial bone graft products, any composite graft, etc.), may be utilized in the present invention.

Inorganic materials, including but not limited to, calcium phosphate materials, and other bone substitute materials, may also be exploited for use as particulate inclusions in the inventive compositions (e.g., composites). Exemplary materials utilized in accordance with the present invention include aragonite, dahlite, calcite, amorphous calcium carbonate, vaterite, weddellite, whewellite, struvite, urate, ferrihydrite, francolite, monohydrocalcite, magnetite, goethite, dentin, calcium carbonate, calcium sulfate, calcium phosphosilicate, sodium phosphate, calcium aluminate, calcium phosphate, hydroxyapatite, α-tricalcium phosphate, dicalcium phosphate, β-tricalcium phosphate, tetracalcium phosphate, amorphous calcium phosphate, octacalcium phosphate, and BIOGLASS™, a calcium phosphate silica glass available from U.S. Biomaterials Corporation. Substituted calcium phosphate phases are also contemplated for use with the invention, including but not limited to fluorapatite, chlorapatite, magnesium-substituted tricalcium phosphate, and carbonate hydroxyapatite. In certain embodiments, the inorganic material is a substituted form of hydroxyapatite. For example, hydroxyapatite may be substituted with other ions such as fluoride, chloride, magnesium, sodium, potassium, and groups such as silicates, silicon dioxides, carbonates, etc. Other calcium phosphate phases suitable for use with the invention include those disclosed in U.S. Pat. Nos. RE 33,161 and RE 33,221 to Brown et al.; U.S. Pat. Nos. 4,880,610; 5,034,059; 5,047,031; 5,053,212; 5,129,905; 5,336,264; and 6,002,065 to Constantz et al.; U.S. Pat. Nos. 5,149,368; 5,262,166 and 5,462,722 to Liu et al.; U.S. Pat. Nos. 5,525,148 and 5,542,973 to Chow et al., U.S. Pat. Nos. 5,717,006 and 6,001,394 to Daculsi et al., U.S. Pat. No. 5,605,713 to Boltong et al., U.S. Pat. No. 5,650,176 to Lee et al., and U.S. Pat. No. 6,206,957 to Driessens et al, and biologically-derived or biomimetic materials such as those identified in Lowenstam H A, Weiner S, *On Biomineralization*, Oxford University Press, 1989; each of which is incorporated herein by reference.

Particulates besides bone particles, such as inorganic materials and/or other bone substitute materials utilized in accordance with the present invention can be treated to enhance their interaction with polymer (e.g., PUR) and/or to confer some properties to particle surface. Surface modification may provide a chemical substance that is adsorbed and/or grafted onto the surface of particulates, e.g., covalently bonded to the surface. Particulates may, alternatively or additionally, be coated with a material to facilitate interaction with polymers of inventive compositions (e.g., composites).

In some embodiments, a particulate composite material may be employed to combine with inventive composites in the present invention. For example, inorganic materials such as those described above may be combined with proteins such as bovine serum albumin (BSA), collagen, or other extracellular matrix components to form a composite. In some embodiments, inorganic materials or bone-derived materials may be combined with synthetic or natural polymers to form a composite using the techniques described in our co-pending U.S. patent applications, U.S. Ser. No. 10/735,135, filed Dec. 12, 2003; U.S. Ser. No. 10/681,651, filed Oct. 8, 2003; and U.S. Ser. No. 10/639,912, filed Aug. 12, 2003, the contents of all of which are incorporated herein by reference.

Other Treatments

Alternatively or additionally, particulates (e.g., bone particles and particulate ceramic biomaterials such as calcium phosphate) utilized in accordance with the present invention can be treated by processes other than defatting and demineralization.

In some embodiments, particulates are treated with polymers. In certain embodiments, non-bone particulates (e.g., inorganic materials and/or other bone substitute materials) can be treated with polymers. For example, treatment can be done by adsorption of polymers (e.g. PEG) and/or by covalent grafting polymers (e.g., polycaprolactone (PCL)) onto particle surface. Hydroxyl groups of suitable polymers (e.g., PEG and PCL) can react with isocyanate groups from polyurethane materials and bind the treated particulates to the polyurethane materials. Without being bound by any particular theory, treated particulates/PUR composites show enhanced mechanical properties (e.g., wet compressive modulus and strengths).

Alternatively or additionally, treated particulates (e.g., bone particles and particulate ceramic biomaterials such as calcium phosphate) utilized in accordance with the present invention can be modified with other agents and/or by other processes. In some embodiments, additional agents and/or processes are used to adjust reactivity of particulates towards polymers (e.g., polyurethane materials). For example, silane coupling agents can employed to link a monomer or initiator molecule (e.g., isocyanates and polyols) to particulates. Silane coupling agents can be used to crosslink particulates. Silane has at least two sections, a set of leaving groups and at least an active group. An active group may be connected to the silicon atom in the silane by an elongated tether group. An exemplary silane coupling agent is 3-trimethoxysilylpropylmethacrylate, available from Union Carbide. Three methoxy groups are leaving groups, and the methacrylate active group is connected to the silicon atom by a propyl tether group. In some embodiments, a leaving group is an alkoxy group such as methoxy or ethoxy. Depending on the solvent used to link a coupling agent to particulates, hydrogen or alkyl groups such as methyl or ethyl may serve as leaving groups. The length of tethers determines the intimacy of connection between polymers and bone particles. By providing a spacer between bone particles and active groups, the tether also reduces competition between chemical groups at the particle surface and the active group and makes the active group more accessible to monomers during polymerization.

In some embodiments, an active group is an analog of monomers of a polymer used in inventive composites. For example, amine active groups will be incorporated into polyurethane matrices, copolymers (e.g., polyesters, polycarbonates, polycaprolactone), and other polymer classes based on monomers that react with amines, even if the polymer does not contain an amine. Hydroxy-terminated silanes will be incorporated into polyamino acids, polyesters, polycaprolactone, polycarbonates, polyurethanes, and other polymer classes that include hydroxylated monomers. Aromatic active groups or active groups with double bonds will be incorporated into vinyl polymers and other polymers that grow by radical polymerization (e.g., polyacrylates, polymethacrylates). It is not necessary that the active group be monofunctional. Indeed, it may be preferable that active groups that are to be incorporated into polymers via step polymerization be difunctional. A silane having two amines, even if one is a secondary amine, will not terminate a polymer chain but can react with ends of two different polymer chains. Alternatively, the active group may be branched to provide two reactive groups in the primary position.

An exemplary list of silanes that may be used with the present invention is provided in U.S. Patent Publication No. 2004/0146543, the contents of which are incorporated herein by reference. Silanes are available from companies such as Union Carbide, AP Resources Co. (Seoul, South Korea), and BASF. Where a silane contains a potentially non-biocompatible moiety as the active group, it may be used to tether a biocompatible compound to bone particles using a reaction in which the non-biocompatible moiety is a leaving group. It may be desirable to attach the biocompatible compound to the silane before attaching the silane to particulates, regardless of whether the silane is biocompatible or not. The derivatized silanes may be mixed with silanes that can be incorporated directly into the polymer and reacted with bone particles, coating the bone particles with a mixture of "bioactive" silanes and "monomer" silanes. U.S. Pat. No. 6,399,693, the contents of which are incorporated herein by reference discloses composites of silane modified polyaromatic polymers and bone. In some embodiments, silane-derivatized polymers may be used in inventive composites instead of or in addition to first silanizing bone particles. In certain embodiments, polyurethanes and any copolymers used in accordance with the present inventions may not include silane modified polyaromatic polymers.

A active group of silanes may be incorporated directly into polymers or may be used to attach a second chemical group to particulates/particles. For example, if a particular monomer polymerizes through a functional group that is not commercially available as a silane, the monomer may be attached to the active group.

Non-silane linkers may also be employed to produce composites according to the invention. For example, isocyanates will form covalent bonds with hydroxyl groups on the surface of hydroxyapatite ceramics (de Wijn, et al., *Fifth World Biomaterials Congress*, May 29-Jun. 2, 1996, Toronto, CA). Isocyanate anchors, with tethers and active groups similar to those described with respect to silanes, may be used to attach monomer-analogs to bone particles or to attach chemical groups that will link covalently or non-covalently with a polymer side group. Polyamines, organic compounds containing one or more primary, secondary, or tertiary amines, will also bind with both the bone particle surface and many monomer and polymer side groups. Polyamines and isocyanates may be obtained from Aldrich.

Alternatively or additionally, biologically active compounds such as a biomolecule, a small molecule, or a bioactive agent may be attached to particles (e.g., bone particles and particulate ceramic biomaterials such as calcium phosphate) through a linker. For example, mercaptosilanes will react with sulfur atoms in proteins to attach them to particles. Aminated, hydroxylated, and carboxylated silanes will react with a wide variety functional groups. Of course, the linker may be optimized for the compound being attached to particulates.

Biologically active molecules can modify non-mechanical properties of inventive composites as they degrade. For example, immobilization of a drug on particles allows it to be gradually released at an implant site as the composite degrades. Anti-inflammatory agents embedded within inventive composites will control inflammatory response long after an initial response to injection of the composites. For example, if a piece of the composite fractures several weeks after injection, immobilized compounds will reduce the intensity of any inflammatory response, and the composite will continue to degrade through hydrolytic or physiological processes. In some embodiments, compounds may also be immobilized on the bone particles that are designed to elicit a particular metabolic response or to attract cells to injection sites.

Some biomolecules, small molecules, and bioactive agents may also be incorporated into polyurethane matrices used in inventive composites. For example, many amino acids have reactive side chains. The phenol group on tyrosine has been exploited to form polycarbonates, polyarylates, and polyiminocarbonates (see Pulapura, et al., *Biopolymers*, 1992, 32:411-417; and Hooper, et al., *J. Bioactive and Compatible Polymers*, 1995, 10:327-340, the entire contents of both of which are incorporated herein by reference). Amino acids such as lysine, arginine, hydroxylysine, proline, and hydroxyproline also have reactive groups and are essentially tri-functional. Amino acids such as valine, which has an isopropyl side chain, are still difunctional. Such amino acids may be attached to the silane and still leave one or two active groups available for incorporation into a polymer.

Non-biologically active materials may also be attached to particles. For example, radiopaque (e.g., barium sulfate), luminescent (e.g., quantum dots), or magnetically active particles (e.g., iron oxide) may be attached to bone particles using the techniques described above. Mineralized bone particles are an inherently radiopaque component of some embodiments of present inventions, whereas demineralized bone particles, another optional component of inventive composites, are not radiopaque. To enhance radiopacity of inventive composites, mineralized bone particles can be used. Another way to render radiopaque the polymers utilized in accordance with the present inventions, is to chemically modify them such that a halogen (e.g., iodine) is chemically incorporated into the polyurethane matrices, as in U.S. patent application Ser. No. 10/952,202, now published as U.S. Patent Publication No. 2006-0034769, whose content is incorporated herein by reference.

If a material, for example, a metal atom or cluster, cannot be produced as a silane or other group that reacts with bone particles, then a chelating agent may be immobilized on bone particle surface and allowed to form a chelate with the atom or cluster. As bone particles and polymers used in the present invention are resorbed, these non-biodegradable materials may be removed from tissue sites by natural metabolic processes, allowing degradation of the polymers and resorption of the bone particles to be tracked using standard medical diagnostic techniques.

In some embodiments, treatments described above or treatments such as etching may be used to increase the surface area or surface roughness of particulates. Such treatments increase the interfacial strength of the particle/polymer interface by increasing the surface area of the interface and/or the mechanical interlocking of particulates and polyurethane. Such treatments may also be employed to round the shape or smooth the edges of particulates to facilitate delivery of the inventive composite. Such treatment is particularly useful for injectable compositions (e.g., composites).

In some embodiments, treatments of particulates are optimized to enhance covalent attractions between particles and polyurethanes. In some embodiments, a treatment may be designed to enhance non-covalent interactions between particulates and polyurethane materials. Exemplary non-covalent interactions include electrostatic interactions, hydrogen bonding, pi-bond interactions, hydrophobic interactions, van der Waals interactions, and mechanical interlocking. For example, if a protein or a polysaccharide is immobilized on a particulate, the chains of polymer matrix will become physically entangled with long chains of the biological macromolecules when they are combined. Charged phosphate sites on the surface of bone particles, produced by washing the bone particles in basic solution, will interact with the amino groups present in many biocompatible polymers, especially those based on amino acids. The pi-orbitals on aromatic groups immobilized on a bone particle will interact with double bonds and aromatic groups of the polymer.

Polymer Component

Synthetic polymers can be designed with properties targeted for a given clinical application. According to the present invention, polyurethane materials (PUR) are a useful class of biomaterials due to the fact that they can be injectable or moldable as a reactive liquid that subsequently cures to form a porous composite. These materials also have tunable degradation rates, which are shown to be highly dependent on the choice of polyol and isocyanate components (Hafeman et al., *Pharmaceutical Research* 2008; 25(10):2387-99; Storey et al., *J Poly Sci Pt A: Poly Chem* 1994; 32:2345-63; Skarja et al., *J App Poly Sci* 2000; 75:1522-34). Polyurethane materials have tunable mechanical properties, which can also be enhanced with the addition of bone particles and/or other components (Adhikari et al., *Biomaterials* 2008; 29:3762-70; Gorna et al., *J Biomed Mater Res Pt A* 2003; 67A(3):813-27) and exhibit elastomeric rather than brittle mechanical properties.

Polyurethane materials can be made by reacting together the components of a two-component composition, which includes a polyisocyanate, and a component having two or more hydroxyl groups (i.e., polyols) to react with the polyisocyanate. Polyurethane materials described in U.S. Ser. No. 12/608,850 filed on Oct. 29, 2009, and published under No. 20100112032, which is entitled "Bone/Polyurethane Composites and Methods Thereof" and incorporated herein by reference, may be used in some embodiments of the present invention.

It is to be understood that by "a two-component composition" it means a composition comprising two essential types of polymer components. In some embodiments, such a composition may additionally comprise one or more other optional components.

In some embodiments, a polyurethane material is a composition that has been rendered formable through combination of two liquid components (i.e., a polyisocyanate prepolymer and a polyol). In some embodiments, a polyisocyanate prepolymer or a polyol may be a molecule with two or three isocyanate or hydroxyl groups respectively. In some embodiments, a polyisocyanate prepolymer or a polyol may have at least four isocyanate or hydroxyl groups respectively.

Polyurethane materials may be prepared by contacting an isocyanate-terminated prepolymer (component 1, e.g., polyisocyanate prepolymer) with a hardener (component 2) that includes at least a polyol (e.g., a polyester polyol) and water, a catalyst and optionally, a stabilizer, a porogen, PEG, etc.

In some embodiments, multiple polyurethanes (e.g., different structures, difference molecular weights) may be used in a composite/composition of the present invention. In some embodiments, other biocompatible and/or biodegradable polymers may be used with polyurethanes in accordance with the present invention. In some embodiments, biocompatible co-polymers and/or polymer blends of any combination thereof may be exploited.

Polyurethane materials used in accordance with the present invention can be adjusted to produce polymers having various physiochemical properties and morphologies including, for example, flexible foams, rigid foams, elastomers, coatings, adhesives, and sealants. The properties of polyurethanes are controlled by choice of the raw materials and their relative concentrations. For example, thermoplastic elastomers are characterized by a low degree of cross-linking and are typically segmented polymers, consisting of alternating hard (diisocyanates and chain extenders) and soft (polyols) segments. Thermoplastic elastomers are formed from the reaction of diisocyanates with long-chain diols and short-chain diol or diamine chain extenders. In some embodiments, pores in bone/polyurethanes composites in the present invention are interconnected and have a diameter ranging from approximately 50 to approximately 1000 microns.

Prepolymer

Polyurethane prepolymers can be prepared by contacting a polyol with an excess (typically a large excess) of a polyisocyanate. The resulting prepolymer intermediate includes an adduct of polyisocyanates and polyols solubilized in an excess of polyisocyanates. Prepolymer can, in some embodiments, be formed by using an approximately stoichiometric amount of polyisocyanates in forming a prepolymer and subsequently adding additional polyisocyanates. The prepolymer therefore exhibits both low viscosity, which facilitates processing, and improved miscibility as a result of the polyisocyanate-polyol adduct. Polyurethane networks can, for example, then be prepared by reactive liquid molding, wherein the prepolymer is contacted with a polyester polyol to form a reactive liquid mixture (i.e., a two-component composition) which is then cast into a mold and cured.

Polyisocyanates or multi-isocyanate compounds for use in the present invention include aliphatic polyisocyanates. Exemplary aliphatic polyisocyanates include, but are not limited to, lysine diisocyanate, an alkyl ester of lysine diisocyanate (for example, the methyl ester or the ethyl ester), lysine triisocyanate, hexamethylene diisocyanate, isophorone diisocyanate (IPDI), 4,4'-dicyclohexylmethane diisocyanate ($H_{12}$MDI), cyclohexyl diisocyanate, 2,2,4-(2,2,4)-trimethylhexamethylene diisocyanate (TMDI), dimers prepared form aliphatic polyisocyanates, trimers prepared from aliphatic polyisocyanates and/or mixtures thereof. In some embodiments, hexamethylene diisocyanate (HDI) trimer sold as Desmodur N3300A may be a polyisocyanate utilized in the present invention. In some embodiments, polyisocyanates used in the present invention includes approximately 10 to 55% NCO by weight (wt % NCO=100* (42/Mw)). In some embodiments, polyisocyanates include approximately 15 to 50% NCO.

Polyisocyanate prepolymers provide an additional degree of control over the structure of biodegradable polyurethanes. Prepared by reacting polyols with isocyanates, NCO-terminated prepolymers are oligomeric intermediates with isocyanate functionality as shown in Scheme 1. To increase reaction rates, urethane catalysts (e.g., tertiary amines) and/or elevated temperatures (60-90° C.) may be used (see, Guelcher, Tissue Engineering: Part B, 14 (1) 2008, pp 3-17).

Polyols used to react with polyisocyanates in preparation of NCO-terminated prepolymers refer to molecules having at least two functional groups to react with isocyanate groups. In some embodiments, polyols have a molecular weight of no more than 1000 g/mol. In some embodiments, polyols have a rang of molecular weight between about 100 g/mol to about 500 g/mol. In some embodiments, polyols have a rang of molecular weight between about 200 g/mol to about 400 g/mol. In certain embodiments, polyols (e.g., PEG) have a molecular weight of about 200 g/mol. Exemplary polyols include, but are not limited to, PEG, glycerol, pentaerythritol, dipentaerythritol, tripentaerythritol, 1,2,4-butanetriol, trimethylolpropane, 1,2,3-trihydroxyhexane, myo-inositol, ascorbic acid, a saccharide, or sugar alcohols (e.g., mannitol, xylitol, sorbitol etc.). In some embodiments, polyols may comprise multiple chemical entities having reactive hydrogen functional groups (e.g., hydroxy groups, primary amine groups and/or secondary amine groups) to react with the isocyanate functionality of polyisocyanates.

In some embodiments, polyisocyanate prepolymers are resorbable. Zhang and coworkers synthesized biodegradable lysine diisocyanate ethyl ester (LDI)/glucose polyurethane materials proposed for tissue engineering applications. In those studies, NCO-terminated prepolymers were prepared from LDI and glucose. The prepolymers were chain-extended with water to yield biocompatible foams which supported the growth of rabbit bone marrow stromal cells in vitro and were non-immunogenic in vivo. (see Zhang, et al., Biomaterials 21: 1247-1258 (2000), and Zhang, et al., Tiss. Eng., 8(5): 771-785 (2002), both of which are incorporated herein by reference).

In some embodiments, prepared polyisocyanate prepolymer can be a flowable liquid at processing conditions. In general, the processing temperature is no greater than 60° C. In some embodiments, the processing temperature is ambient temperature (25° C.).

Polyols

Polyols utilized in accordance with the present invention can be amine- and/or hydroxyl-terminated compounds and include, but are not limited to, polyether polyols (such as polyethylene glycol (PEG or PEO), polytetramethylene etherglycol (PTMEG), polypropylene oxide glycol (PPO)); amine-terminated polyethers; polyester polyols (such as polybutylene adipate, caprolactone polyesters, castor oil); and polycarbonates (such as poly(1,6-hexanediol) carbonate). In some embodiments, polyols may be (1) molecules having multiple hydroxyl or amine functionality, such as glucose, polysaccharides, and castor oil; and (2) molecules (such as fatty acids, triglycerides, and phospholipids) that have been hydroxylated by known chemical synthesis techniques to yield polyols.

Polyols used in the present invention may be polyester polyols. In some embodiments, polyester polyols may include polyalkylene glycol esters or polyesters prepared from cyclic esters. In some embodiments, polyester polyols may include poly(ethylene adipate), poly(ethylene glutarate), poly(ethylene azelate), poly(trimethylene glutarate), poly(pentamethylene glutarate), poly(diethylene glutarate), poly(diethylene adipate), poly(triethylene adipate), poly(1,2-propylene adipate), mixtures thereof, and/or copolymers thereof. In some embodiments, polyester polyols can include, polyesters prepared from caprolactone, glycolide, D, L-lactide, mixtures thereof, and/or copolymers thereof. In some embodiments, polyester polyols can, for example, include polyesters prepared from castor-oil. When polyurethanes degrade, their degradation products can be the polyols from which they were prepared from.

In some embodiments, polyester polyols can be miscible with prepared prepolymers used in reactive liquid mixtures (i.e., two-component composition) of the present invention. In some embodiments, surfactants or other additives may be included in the reactive liquid mixtures to help homogenous mixing.

The glass transition temperature (Tg) of polyester polyols used in the reactive liquids to form polyurethanes can be less than 60° C., less than 37° C. (approximately human body temperature) or even less than 25° C. In addition to affecting flowability at processing conditions, Tg can also affect degradation. In general, a Tg of greater than approximately 37° C. will result in slower degradation within the body, while a Tg below approximately 37° C. will result in faster degradation.

Molecular weight of polyester polyols used in the reactive liquids to form polyurethanes can, for example, be adjusted to control the mechanical properties of polyurethanes utilized in accordance with the present invention. In that regard, using polyester polyols of higher molecular weight results in greater compliance or elasticity. In some embodiments, polyester polyols used in the reactive liquids may have a molecular weight less than approximately 3000 Da. In certain embodiments, the molecular weight may be in the range of approximately 200 to 2500 Da or 300 to 2000 Da. In some embodiments, the molecular weight may be approximately in the range of approximately 450 to 1800 Da or 450 to 1200 Da.

In some embodiments, a polyester polyol comprise poly (caprolactone-co-lactide-co-glycolide), which has a molecular weight in a range of 200 Da to 2500 Da, or 300 Da to 2000 Da.

In some embodiments, polyols may include multiply types of polyols with different structures, molecular weight, properties, etc.

Additional Components

In accordance with the present invention, two-component compositions (i.e., polyprepolymers and polyols) to form porous composites may be used with other agents and/or catalysts. Zhang et al. have found that water may be an adequate blowing agent for a lysine diisocyanate/PEG/glycerol polyurethane (see Zhang, et al., Tissue Eng. 2003 (6):1143-57) and may also be used to form porous structures in polyurethanes. Other blowing agents include dry ice or other agents that release carbon dioxide or other gases into the composite. Alternatively, or in addition, porogens (see detail discussion below) such as salts may be mixed in with reagents and then dissolved after polymerization to leave behind small voids.

Two-component compositions and/or the prepared composites used in the present invention may include one or more additional components. In some embodiments, inventive compositions and/or composites may includes, water, a catalyst (e.g., gelling catalyst, blowing catalyst, etc.), a stabilizer, a plasticizer, a porogen, a chain extender (for making of polyurethanes), a pore opener (such as calcium stearate, to control pore morphology), a wetting or lubricating agent, etc. (See, U.S. Ser. No. 10/759,904 published under No. 2005-0013793, and U.S. Ser. No. 11/625,119 published under No. 2007-0191963; both of which are incorporated herein by reference).

In some embodiments, inventive compositions and/or composites may include and/or be combined with a solid filler (e.g., carboxymethylcellulose (CMC) and hyaluronic acid (HA)). For example, when composites used in wound healing, solid particulates can help absorb excess moisture in the wounds from blood and serum and allow for proper foaming.

In certain embodiments, additional biocompatible polymers (e.g., PEG) or co-polymers can be used with compositions and composites in the present invention.

In some embodiments, at least one catalyst is added to form reactive liquid mixture (i.e., two-component compositions). A catalyst, for example, can be non-toxic (in a concentration that may remain in the polymer).

A catalyst can, for example, be present in two-component compositions in a concentration in the range of approximately 0.5 to 5 parts per hundred parts polyol (pphp) and, for example, in the range of approximately 0.5 to 2, or 2 to 3 pphp. A catalyst can, for example, be an amine compound. In some embodiments, catalyst may be an organometallic compound or a tertiary amine compound. In some embodiments the catalyst may be stannous octoate (an organobismuth compound), triethylene diamine, bis(dimethylaminoethyl)ether, dimethylethanolamine, dibutyltin dilaurate, and Coscat organometallic catalysts manufactured by Vertullus (a bismuth based catalyst), or any combination thereof.

Components to be Delivered

Alternatively or additionally, composites of the present invention may have one or more components to be delivered when implanted, including biomolecules, small molecules, bioactive agents, etc., to promote bone growth and connective tissue regeneration, and/or to accelerate healing. Examples of materials that can be incorporated include chemotactic factors, angiogenic factors, bone cell inducers and stimulators, including the general class of cytokines such as the TGF-β superfamily of bone growth factors, the family of bone morphogenic proteins, osteoinductors, and/or bone marrow or bone forming precursor cells, isolated using standard techniques. Sources and amounts of such materials that can be included are known to those skilled in the art.

Biologically active materials, comprising biomolecules, small molecules, and bioactive agents may also be included in inventive composites to, for example, stimulate particular metabolic functions, recruit cells, or reduce inflammation. For example, nucleic acid vectors, including plasmids and viral vectors, that will be introduced into the patient's cells and cause the production of growth factors such as bone morphogenetic proteins may be included in a composite. Biologically active agents include, but are not limited to, antiviral agent, antimicrobial agent, antibiotic agent, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, anti-rejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, hydroxyapatite, and penetraction enhancer. Additional exemplary substances include chemotactic factors, angiogenic factors, analgesics, antibiotics, anti-inflammatory agents, bone morphogenic proteins, and other growth factors that promote cell-directed degradation or remodeling of the polymer phase of the composite and/or development of new tissue (e.g., bone). RNAi or other technologies may also be used to reduce the production of various factors.

In some embodiments, inventive composites include antibiotics. Antibiotics may be bacteriocidial or bacteriostatic. An anti-microbial agent may be included in composites. For example, anti-viral agents, anti-protazoal agents, anti-parasitic agents, etc. may be include in composites. Other suitable biostatic/biocidal agents include antibiotics, povidone, sugars, and mixtures thereof. Exemplary antibiotics include, but not limit to, Amikacin, Gentamicin, Kanamycin, Neomycin, Netilmicin, Streptomycin, Tobramycin, Paromomycin, Geldanamycin, Herbimycin, Loravabef, etc. (See, *The Merck Manual of Medical Information—Home Edition*, 1999).

Inventive composites may also be seeded with cells. In some embodiments, a patient's own cells are obtained and used in inventive composites. Certain types of cells (e.g., osteoblasts, fibroblasts, stem cells, cells of the osteoblast lineage, etc.) may be selected for use in the composite. Cells may be harvested from marrow, blood, fat, bone, muscle, connective tissue, skin, or other tissues or organs. In some embodiments, a patient's own cells may be harvested, optionally selected, expanded, and used in the inventive composite. In other embodiments, a patient's cells may be harvested, selected without expansion, and used in the inventive composite. Alternatively, exogenous cells may be employed. Exemplary cells for use with the invention include mesenchymal stem cells and connective tissue cells, including osteoblasts, osteoclasts, fibroblasts, preosteoblasts, and partially differentiated cells of the osteoblast lineage. Cells may be genetically engineered. For example, cells may be engineered to produce a bone morphogenic protein.

In some embodiments, inventive composites may include a composite material comprising a component to be delivered. For example, a composite materials can be a biomolecule (e.g., a protein) encapsulated in a polymeric microsphere or nanoparticles. In certain embodiments, BMP-2 encapsulated in PLGA microspheres may be embedded in a bone/polyurethane composite used in accordance with the present invention. Sustained release of BMP-2 can be achieved due to the diffusional barriers presented by both the PLGA and Polyurethane of the inventive composite. Thus, release kinetics of growth factors (e.g., BMP-2) can be tuned by varying size of PLGA microspheres and porosity of polyurethane composite.

To enhance biodegradation in vivo, composites of the present invention can also include different enzymes. Examples of suitable enzymes or similar reagents are proteases or hydrolases with ester-hydrolyzing capabilities. Such enzymes include, but are not limited to, proteinase K, bromelaine, pronase E, cellulase, dextranase, elastase, plasmin streptokinase, trypsin, chymotrypsin, papain, chymopapain, collagenase, subtilisin, chlostridopeptidase A, ficin, carboxypeptidase A, pectinase, pectinesterase, an oxireductase, an oxidase, or the like. The inclusion of an appropriate amount of such a degradation enhancing agent can be used to regulate implant duration.

Components to be delivered may not be covalently bonded to a component of the composite. In some embodiments, components may be selectively distributed on or near the surface of inventive composites using the layering techniques described above. While surface of inventive composite will be mixed somewhat as the composite is manipulated in implant site, thickness of the surface layer will ensure that at least a portion of the surface layer of the composite remains at surface of the implant. Alternatively or in addition, biologically active components may be covalently linked to the bone particles before combination with the polymer. As discussed above, for example, silane coupling agents having amine, carboxyl, hydroxyl, or mercapto groups may be attached to the bone particles through the silane and then to reactive groups on a biomolecule, small molecule, or bioactive agent.

Preparation of Compositions/Composites

In general, inventive compositions (e.g., composites) are prepared by combining particles, polymers and optionally any additional components. To form inventive compositions (e.g., composites), particles as discussed herein may be combined with a reactive liquid (i.e., a two-component composition) thereby forming an injectable or moldable composite or a composite that can be made injectable or moldable. Alternatively, particles may be combined with polyisocyanate prepolymers or polyols first and then combined with other components.

In some embodiments, particles may be combined first with a hardener that includes polyols, catalysts and optionally a solvent, a stabilizer, a porogen, a plasticizer, etc., and then combined with a polyisocyanate prepolymer. In some embodiments, a hardener (e.g., at least one polyol, and at least one catalyst) may be mixed with at least one prepolymer, followed by addition of particles. In some embodiments, in order to enhance storage stability of two-component compositions, the two (liquid) component process may be modified to an alternative three (liquid)-component process wherein a catalyst and water may be dissolved in a solution separating from reactive polyols. For example, polyester polyols may be first mixed with at least one catalyst, followed by addition of particles, and finally addition of NCO-terminated prepolymers.

In some embodiments, additional components or components to be delivered may be combined with a reactive liquid prior to injection. In some embodiments, they may be combined with one of polymer precursors (i.e., prepolymers and polyols) prior to mixing the precursors in forming of a reactive liquid/paste.

Various compositions can be prepared using a small amount of catalysts to assist forming composites. In general, the more blowing catalyst used, the high porosity of inventive composites may be achieved.

Polymers and particles may be combined by any method known to those skilled in the art. For example, a homogenous mixture of polymers and/or polymer precursors (e.g., prepolymers, polyols, etc.) and particles may be pressed together at ambient or elevated temperatures. At elevated temperatures, a process may also be accomplished without pressure. In some embodiments, polymers or precursors are not held at a temperature of greater than approximately 60° C. for a significant time during mixing to prevent thermal damage to any biological component (e.g., growth factors or cells) of a composite. In some embodiments, temperature is not a concern because particles and polymer precursors used in the present invention have a low reaction exotherm.

Alternatively or in addition, particles may be mixed or folded into a polymer softened by heat or a solvent. Alternatively, a moldable polymer may be formed into a sheet that is then covered with a layer of particles. Particles may then be forced into the polymer sheet using pressure. In another embodiment, particles are individually coated with polymers or polymer precursors, for example, using a tumbler, spray coater, or a fluidized bed, before being mixed with a larger quantity of polymer. This facilitates even coating of the particles and improves integration of particles and polymer components of the compositions.

Upon combination with particles, polymers may undergo cross-linking or polymerization to form a composite in which the polymer is covalently linked to the particles. In some embodiments, compositions harden in a solvent-free condition. In some embodiments, compositions are a polymer/solvent mixture that hardens when a solvent is removed (e.g., when a solvent is allowed to evaporate or diffuse away). Exemplary solvents include but are not limited to alcohols (e.g., methanol, ethanol, propanol, butanol, hexanol, etc.), water, saline, DMF, DMSO, glycerol, and PEG. In certain embodiments, a solvent is a biological fluid such as blood, plasma, serum, marrow, etc. In certain embodiments, an inventive composite is heated above the melting or glass transition temperature of one or more of its components and becomes set after implantation as it cools. In certain embodiments, an inventive composite is set by exposing a composite to a heat source, or irradiating it with microwaves, IR rays, or UV light. Particles may also be mixed with a polymer that is sufficiently pliable to combine with the particles but that may require further treatment, for example, combination with a solvent or heating, to become a injectable or moldable composition. For example, a composition may be combined and injection molded, injected, extruded, laminated, sheet formed, foamed, or processed using other techniques known to those skilled in the art. In some embodiments, reaction injection molding methods, in which polymer precursors (e.g., polyisocyanate prepolymer, a polyol) are separately charged into a mold under precisely defined conditions, may be employed. For example, bone particles may be added to a precursor, or it may be separately charged into a mold and precursor materials added afterwards. Careful control of relative amounts of various components and reaction conditions may be desired to limit the amount of unreacted material in a composite. Post-cure processes known to those skilled in the art may also be employed. A partially polymerized polyurethane precursor may be more completely polymerized or cross-linked after combination with hydroxylated or aminated materials or included materials (e.g., a particulate, any components to be delivered, etc.).

In some embodiments, an inventive composite is produced with a injectable composition and then set in situ. For example, cross-link density of a low molecular weight polymer may be increased by exposing it to electromagnetic radiation (e.g., UV light) or an alternative energy source. Alternatively or additionally, a photoactive cross-linking agent, chemical cross-linking agent, additional monomer, or combinations thereof may be mixed into inventive composites. Exposure to UV light after a composition is injected into an implant site will increase one or both of molecular weight and cross-link density, stiffening polymers (i.e., polyurethanes) and thereby a composite. Polymer components of inventive composites used in the present invention may be softened by a solvent, e.g., ethanol. If a biocompatible solvent is used, polyurethanes may be hardened in situ. In some embodiments, as a composite sets, solvent leaving the composite is released into surrounding tissue without causing undesirable side effects such as irritation or an inflammatory response. In some embodiments, compositions utilized in the present invention becomes moldable at an elevated temperature into a pre-determined shape. Composites may become set when composites are implanted and allowed to cool to body temperature (approximately 37° C.).

The present invention also provides methods of preparing inventive compositions by combining bone particles and polyurethane precursors and resulting in flowable compositions. Alternatively or additionally, the invention provides methods to make a porous composite include adding a solvent or pharmaceutically acceptable excipient to render a flowable or moldable composition. Such a composition may then be injected or placed into the site of implantation. As solvent or excipient diffuses out of the composite, it may become set in place.

Polymer processing techniques may also be used to combine particles with a polyurethane or precursors (e.g., polyisocyanates and polyols). In some embodiments, a composition of polyurethane may be rendered formable (e.g., by heating or with a solvent) and combined with particles by injection molding or extrusion forming. Alternatively, polyurethanes and bone particles may be mixed in a solvent and cast with or without pressure. For example, a solvent may be dichloromethane. In some embodiments, a composition of particle and polymer utilized in the present invention is naturally injectable or moldable in a solvent-free condition.

In some embodiments, particles may be mixed with a polymer precursor according to standard composite processing techniques. For example, regularly shaped particles may simply be suspended in a precursor. A polymer precursor may be mechanically stirred to distribute the particles or bubbled with a gas, preferably one that is oxygen- and moisture-free. Once components of a composition are mixed, it may be desirable to store it in a container that imparts a static pressure to prevent separation of the particles and the polymer precursor, which may have different densities. In some embodiments, distribution and particle/polymer ratio may be optimized to produce at least one continuous path through a composite along particles.

Interaction of polymer components with bone particles may also be enhanced by coating individual particles with a polymer precursor before combining them with bulk precursors. The coating enhances the association of the polymer component of the composite with the particles. For example, individual particles may be spray coated with a monomer or prepolymer. Alternatively, the individual particles may be coated using a tumbler—particles and a solid polymer material are tumbled together to coat the particles. A fluidized bed coater may also be used to coat the particles. In addition, the particles may simply be dipped into liquid or powdered polymer precursor. All of these techniques will be familiar to those skilled in the art.

In some embodiments, it may be desirable to infiltrate a polymer or polymer precursor into vascular and/or interstitial structure of bone particles or into bone-derived tissues. Vascular structure of bone includes such structures such as osteocyte lacunae, Haversian canals, Volksmann's canals, canaliculi and similar structures. Interstitial structure of bone particles includes spaces between trabeculae and similar features. Many of monomers and precursors (e.g., polyisocyanate prepolymers, polyols) suggested for use with the invention are sufficiently flowable to penetrate through the channels and pores of trabecular bone. Some may even penetrate into trabeculae or into mineralized fibrils of cortical bone. Thus, it may be necessary to incubate bone particles in polyurethane precursors for a period of time to accomplish infiltration. In certain embodiments, polyurethane itself is sufficiently flowable that it can penetrate channels and pores of bone. In certain embodiments, polyurethane may also be heated or combined with a solvent to make it more flowable for this purpose. Other ceramic materials and/or other bone-substitute materials employed as a particulate phase may also include porosity that can be infiltrated as described herein.

Inventive compositions (e.g., composites) utilized in according to the present invention may include practically any ratio of polymer components (e.g., polyols, and prepolymers) and particulate components. Each component can be treated (e.g., surface modified) in order to adjust resulting properties of such compositions (e.g., composites). For example, a kinetic rate for reaction with isocyanate prepolymers is a characteristic of certain components (e.g., polyol, particles such as bone particles or inorganic particles). In some embodiments, provided compositions comprise defatted bone particles that have a specific reaction rate relative to water of 5-7 g mol$^{-1}$ sec$^{-1}$ at 23° C. (e.g., a kinetic rate defined in Example 3). In some embodiments, provided compositions comprise defatted bone particles that have a specific reaction rate relative to water at 23° C. of at least 1 g mol$^{-1}$ sec$^{-1}$ and less than 10 g sec$^{-1}$.

In some embodiments, a relative kinetic rate for reaction with isocyanate prepolymers (defined by the kinetic rate of a particulate component (e.g., bone particles and/or inorganic particulates) divided by that of a polyol) in a composition is about 0.01, 0.02, 0.05, 0.1, 0.2, 0.3, 0.4, 0.5, 0.6, 0.8, 1, 2, and 5. In some embodiments, a relative kinetic rate for reaction with isocyanate prepolymers in a composition is in a range of any two values above. In some embodiments, a relative kinetic rate for reaction with isocyanate prepolymers in a composition is in a range of 0.1-0.6. In some embodiments, a kinetic rate of the particulate material for reaction with isocyanate prepolymers is about 0.1-0.6 times of that of the polyol.

In some embodiments, a provided composition comprises defatted bone particles that have an index (defined as a ratio of isocyanate and hydroxyl equivalents multiplied by 100) of about 100, 110, 120, 130, 140, and 150. In some embodiments, a provided composition comprises defatted bone particles that have an index in a range of any two values above. In some embodiments, a provided composition comprises defatted bone particles that have an index in a range of 100-120, or 110-115.

Inventive compositions (e.g., composites) utilized in according to the present invention may include practically any ratio of polyurethane materials and particulate materials. In some embodiments, compositions may include at least approximately 30 vol %, 35 vol %, 40 vol %, or 50 vol % of particles. In some embodiments, a volume percentage of particles in a composition in accordance with the present invention may be about 30 vol %, 35 vol %, 40 vol %, 50 vol %, 60 vol %, 70 vol % or between any volume percentages of above. In some embodiments, a composition in accordance with the present invention may have a volume percentage (fraction) of bone particles and/or other particulate materials (e.g., calcium phosphate) in a range of about 50-60 vol %. In some embodiments, a composition in accordance with the present invention may have a volume percentage (fraction) of at least approximately 55 vol % of particles (e.g., bone particles and/or other particulate materials). In some embodiments, a composition in accordance with the present invention may have a volume percentage (fraction) of at least approximately 50-60 vol % of defatted bone particles. In some embodiments, a composition in accordance with the present invention may have a volume percentage (fraction) of at least approximately 55 vol % of defatted bone particles. In some embodiments, volume percentages (fractions) of bone particles and/or other particulate materials in porous composites in the present invention may be less than 64 vol %. In certain embodiments, for a certain volume percentage, corresponding weight percentage of bone particles and/or other particulate materials varies depending on density of particulate components.

Desired proportion may depend on factors such as injection sites, shape and size of the particles, how evenly polymer is distributed among particles, desired flowability of composites, desired handling of composites, desired moldability of composites, and mechanical and degradation properties of composites. The proportions of polymers and particles can influence various characteristics of the composite, for example, its mechanical properties, including fatigue strength, the degradation rate, and the rate of biological incorporation. In addition, the cellular response to the composite will vary with the proportion of polymer and particles. In some embodiments, the desired proportion of particles may be determined not only by the desired biological properties of the injected material but by the desired mechanical properties of the injected material. That is, an increased proportion of particles will increase the viscosity of the composite, making it more difficult to inject or mold. A larger proportion of particles having a wide size distribution may give similar properties to a mixture having a smaller proportion of more evenly sized particles.

Provided composites of the present invention can exhibit a degree of porosity over a wide range of effective pore sizes. In some embodiments, provided composite has a porosity less than about 15%. In some embodiments, provided composites have a porosity less than about 10%, 5%, 3% or 2%. Pores in compositions/composites can facilitate cellular and tissue in-growth into the composite, more continuous supply of nutrients, more thorough infiltration of therapeutics, and enhanced revascularization, allowing bone growth and repair to take place more efficiently. Furthermore, in certain embodiments, pores of compositions/composite may be used to load the composite with biologically active agents such as drugs, small molecules, cells, peptides, polynucleotides, growth factors, osteogenic factors, etc, for delivery at the implant site.

In some embodiments, wet compressive strength of provided compositions/composites is in an approximate range of 5-100 MPa, or 10-60 MPa. In some embodiments, wet compressive modulus of provided compositions/composites is in an approximate range of 300-3000 MPa, or 600-2000 MPa. In some embodiments, yield strain of provided compositions/composites is more than 1%, or more than 3%. In some embodiments, swelling of provided compositions/composites is less than 15%, or less than 8%.

Surprisingly, in some embodiments, wet compressive modulus of provided composites comprising defatted bone particles is at least 1.5, 2, or 3 times higher than that observed with otherwise comparable composites lacking defatted bone particles. In some embodiments, wet compressive strength of a provided composites comprising defatted bone particles is at least 1.5, 2, or 3 times higher than that observed with otherwise comparable composites lacking defatted bone particles.

After implantation, inventive composites are allowed to remain at the site providing the strength desired while at the same time promoting healing of the bone and/or bone growth. Polyurethane of composites may be degraded or be resorbed as new bone is formed at the implantation site. Polymer may be resorbed over approximately 1 month to approximately 1 years. For example, polyurethane materials used in accordance with the present invention may be resorbed completely within about 4-8 weeks, 2-6 months, or 6-12 months. In some embodiments, polyurethane materials used in accordance with the present invention may be resorbed completely within about 3 months. A degradation rate is defined as the mass loss as a function of time, and it can be measured by immersing the sample in phosphate buffered saline or medium and measuring the sample mass as a function of time. Additionally or alternatively, composites may start to be remodeled in as little as a week as the composite is infiltrated with cells or new bone in-growth. A remodeling process may continue for weeks, months, or years. For example, particulate materials used in accordance with the present invention may be remodeled by 50% within about 4-6 weeks, 6-8 weeks, 8-12 weeks, 12-24 weeks, 2-6 months, or 6-12 months. In some embodiments, particulate materials used in accordance with the present invention may be remodeled by 50% within about 1, 2, or 3 months.

One skilled in the art will recognize that standard experimental techniques may be used to test these properties for a range of compositions to optimize a composite for a desired application. For example, standard mechanical testing instruments may be used to test the compressive strength and stiffness of composites. Cells may be cultured on composites for an appropriate period of time, and metabolic products and amount of proliferation (e.g., the number of cells in comparison to the number of cells seeded) may be analyzed. Weight change of composites may be measured after incubation in saline or other fluids. Repeated analysis will demonstrate whether degradation of a composite is linear or not, and mechanical testing of incubated materials will show changes in mechanical properties as a composite degrades. Such testing may also be used to compare enzymatic and non-enzymatic degradation of a composite and to determine levels of enzymatic degradation. A composite that is degraded is transformed into living bone upon implantation.

Use and Application of Composite

As discussed above, polymers or polymer precursors, and particles may be supplied separately, e.g., in a kit, and mixed immediately prior to implantation, injection or molding. A kit may contain a preset supply of bone particles having, e.g., certain sizes, shapes, and levels of demineralization. Surface of bone particles may have been optionally modified using one or more of techniques described herein. Alternatively, a kit may provide several different types of particles of varying sizes, shapes, and levels of demineralization and that may have been chemically modified in different ways. A surgeon or other health care professional may also combine components in a kit with autologous tissue derived during surgery or biopsy. For example, a surgeon may want to include autogenous tissue or cells, e.g., bone marrow or bone shavings generated while preparing a implant site, into a composite (see more details in co-owned U.S. Pat. No. 7,291,345 and U.S. Ser. No. 11/625,119 published under No. 2007-0191963; both of which are incorporated herein by reference).

Composites of the present invention may be used in a wide variety of clinical applications. A method of preparing and using polyurethanes for orthopedic applications utilized in the present invention may include the steps of providing a curable bone/polyurethane composition, mixing parts of a composition, and curing a composition in a tissue site wherein a composition is sufficiently flowable to permit injection by minimally invasive techniques. In some embodiments, a flowable composition to inject may be pressed by hand or machine. In some embodiments, a moldable composition may be pre-molded and implanted into a target site. Injectable or moldable compositions utilized in the present invention may be processed (e.g., mixed, pressed, molded, etc.) by hand or machine.

Inventive composites and/or compositions may be used as injectable materials with or without exhibiting high mechanical strength (i.e., load-bearing or non-load bearing, respectively). In some embodiments, inventive composites and/or compositions may be used as moldable materials. For example, compositions (e.g., prepolymer, monomers, reactive liquids/pastes, polymers, bone particles, additional components, etc.) in the present invention can be pre-molded into pre-determined shapes. Upon implantation, the pre-molded composite may further cure in situ and provide mechanical strength (i.e., load-bearing). A few examples of potential applications are discussed in more detail below.

In some embodiments, compositions and/or composites of the present invention may be used as a bone void filler. Bone fractures and defects, which result from trauma, injury, infection, malignancy or developmental malformation can be difficult to heal in certain circumstances. If a defect or gap is larger than a certain critical size, natural bone is unable to bridge or fill the defect or gap. These are several deficiencies that may be associated with the presence of a void in a bone. Bone void may compromise mechanical integrity of bone, making bone potentially susceptible to fracture until void becomes ingrown with native bone. Accordingly, it is of interest to fill such voids with a substance which helps voids to eventually fill with naturally grown bone. Open fractures and defects in practically any bone may be filled with composites according to various embodiments without the need for periosteal flap or other material for retaining a composite in fracture or defect. Even where a composite is not required to bear weight, physiological forces will tend to encourage remodeling of a composite to a shape reminiscent of original tissues.

Many orthopedic, periodontal, neurosurgical, oral and maxillofacial surgical procedures require drilling or cutting into bone in order to harvest autologous implants used in procedures or to create openings for the insertion of implants. In either case voids are created in bones. In addition to all the deficiencies associated with bone void mentioned above, surgically created bone voids may provide an opportunity for incubation and proliferation of any infective agents that are introduced during a surgical procedure. Another common side effect of any surgery is ecchymosis in surrounding tissues which results from bleeding of the traumatized tissues. Finally, surgical trauma to bone and surrounding tissues is known to be a significant source of post-operative pain and inflammation. Surgical bone voids are sometimes filled by the surgeon with autologous bone chips that are generated during trimming of bony ends of a graft to accommodate graft placement, thus accelerating healing. However, the volume of these chips is typically not sufficient to completely fill the void. Composites and/or compositions of the present invention, for example composites comprising anti-infective and/or anti-inflammatory agents, may be used to fill surgically created bone voids.

Inventive composites may be administered to a subject in need thereof using any technique known in the art. A subject is typically a patient with a disorder or disease related to bone. In certain embodiments, a subject has a bony defect such as a fracture. In some embodiment, a subject is typically a mammal although any animal with bones may benefit from treatment with the inventive composite. In certain embodiments, a subject is a vertebrate (e.g., mammals, reptiles, fish, birds, etc.). In certain embodiments, a subject is a human. In other embodiments, the subject is a domesticated animal such as a dog, cat, horse, etc. Any bone disease or disorder may be treated using inventive composites/compositions including genetic diseases, congenital abnormalities, fractures, iatrogenic defects, bone cancer, bone metastases, inflammatory diseases (e.g., rheumatoid arthritis), autoimmune diseases, metabolic diseases, and degenerative bone disease (e.g., osteoarthritis). In certain embodiments, inventive osteoimplant composites are formulated for repair of a simple fracture, compound fracture, or non-union; as an external fixation device or internal fixation device; for joint reconstruction, arthrodesis, arthroplasty, or cup arthroplasty of hips; for femoral or humeral head replacement; for femoral head surface replacement or total joint replacement; for repair of vertebral column, spinal fusion or internal vertebral fixation; for tumor surgery; for deficit filling; for discectomy; for laminectomy; for excision of spinal tumors; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; and, for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones, or metatarsal bones, and for repair of bone surrounding cysts and tumors.

Composites and/or compositions of the present invention can be used as bone void fillers either alone or in combination with one or more other conventional devices, for example, to fill the space between a device and bone. Examples of such devices include, but are not limited to, bone fixation plates (e.g., cranofacial, maxillofacial, orthopedic, skeletal, and the like); screws, tacks, clips, staples, nails, pins or rods, anchors (e.g., for suture, bone, and the like), scaffolds, scents, meshes (e.g., rigid, expandable, woven, knitted, weaved, etc), sponges, implants for cell encapsulation or tissue engineering, drug delivery (e.g., carriers, bone ingrowth induction catalysts such as bone morphogenic proteins, growth factors (e.g., PDGF, VEGF and BMP-2), peptides, antivirals, antibiotics, etc), monofilament or multifilament structures, sheets, coatings, membranes (e.g., porous, microporous, resorbable, etc), foams (e.g., open cell or close cell), screw augmentation, cranial, reconstruction, and/or combinations thereof.

These and other aspects of the present invention will be further appreciated upon consideration of the following Examples, which are intended to illustrate certain particular embodiments of the invention but are not intended to limit its scope, as defined by the claims.

EXAMPLES

Example 1

1.1. Materials

Lysine triisocyanate (LTI) was purchased from Kyowa Hakko USA (New York) and polyethylene glycol (PEG, MW 300 and 8000 Da) from Alfa Aesar (Ward Hill, Mass.). Glycerol, ε-caprolactone, stannous octate, hydrochloric acid, phosphoric acid, chloroform, and the reagents for the alkaline phosphatase assay were obtained from Sigma-Aldrich (St. Louis, Mo.). Glycolide and D,L-lactide were purchased from Polysciences (Warrington, Pa.). The tertiary amine catalyst (TEGOAMIN33) was obtained as a gift from Goldschmidt (Hopewell, Va.). Mineralized bone was received as a gift by Osteotech (Eatontown, N.J.) and β-TriCalcium Phosphate (β-TCP, grain size distribution 100-300 μm) was purchased from Berkeley Advanced Biomaterials (Berkeley, Calif.). MC3T3 mouse calvarial osteoprogenitor cells were obtained from American Type Culture Collection (Manassas, Va.) and cultured in complete media: α-MEM supplemented with 10% fetal bovine serum (FBS) and 1% penicillin/streptomycin, all supplied by Fisher Scientific. Phosphate buffered saline (PBS) was purchased from Invitrogen and Borate buffer. The Live/Dead Viability/Cytotoxicity Kit and CyQUANT Cell proliferation Assay Kit were purchased from Invitrogen. Prior to use, glycerol and PEG were dried at 10 mmHg for 3 h at 80° C., and ε-caprolactone was dried over anhydrous magnesium sulfate [4]. All other materials were used as received.

1.2. Methods 1.2.1. Synthesis of prepolymers and polyols.

Previously published techniques were applied to prepare the polyol[5, 6] and the NCO-terminated prepolymer[7]. These materials were used to obtain the polyurethane network in the composites. A trifunctional polyester polyol (300 g/mol) was prepared from a glycerol starter and a 60% ε-caprolactone, 30% glycolide, 10% D,L-lactide backbone using a stannous octoate catalyst (0.1 wt %). An LTI-PEG prepolymer was prepared from poly(ethylene glycol) (PEG, 200 g/mol) with a molar ratio of 2:1 (NCO:OH equivalent ratio=3:1) and NCO number of 22.2%. The OH number of the polyol (used to determine the molecular weight) and the % NCO number of the pre-polymer were measured by titration using a Metrohm 798 MPT Titrino according to ASTM D4274-99 Method C and ASTM D2572-97 respectively. The properties of the prepolymer have been reported previously [7].

1.2.2. Characterization of Allograft Bone Particles

The skeletal density, which accounts for both the volume of the solid as well as the blind (e.g., inaccessible) pores of TCP and allograft bone particles was measured by gas pycnometry using nitrogen as the penetrating gas (Micromeritics, Norcross, Ga.). The particle size distribution of these particles was measured using a Saturn DigiSizer 5200 V1.12 (Micromeritics, Norcross, Ga.). The particle size distribution was determined from scanning electron microscopy pictures using the MetaMorph 7.1.0.0 software.

1.2.3. Surface Modification of Mineralized Bone Particles (MBP)

To obtain defatted bone (DFMBP), mineralized bone particles were stirred with a 50/50% volume solution of acetone/chloroform in a volumetric ratio of 1:10 for at least 48 h. The defatted bone was then washed with acetone and lyophilized for 48 h. Surface demineralized bone (SDMBP) was prepared by acid etching [8]. Briefly, defatted bone was incubated in 0.1 M HCl, sonicated, and washed with distilled water. After washing with deionized water the etching step with HCl was repeated. Finally, the product was lyophilized for a minimum of 48 h.

1.2.4. Coating of Allograft Bone Particles with Methoxy Phenyl Isothiocyanate

In order to test the effects of interfacial binding on the mechanical properties of allograft/PUR composites, b-DFMBP was prepared by reacting DFMBP with 4-methoxyphenyl isothiocyanate, which was anticipated to block the allograft from reacting with PUR during the composite fabrication process. Briefly, DFMBP was dispersed in dimethyl sulfoxide (DMSO) and contacted with 4-methoxyphenyl isothiocyanate and 1000 ppm stannous octoate at 60° C. overnight. The resulting b-DFMBP was subsequently filtered, washed 3× with DI water, washed with ethanol, and dried under vacuum at room temperature for 3 days.

1.2.5. X-Ray Photoelectron Spectroscopy (XPS)

The surface composition of the allograft bone particles was assessed using a PHI 5000 VersaProbe XPS with a 25W monochromatic Al K-α X-ray source and a 100 μm spot size. Survey spectra were collected using 187.85 pass energy. All measurements were performed using a 45° take-off angle and charge neutralization under ultra-high vacuum. Analysis of the data was performed using the software CasaXPS Version 2.3.14 (© 1999-2008 Neal Fairley).

1.2.6. Allograft/PUR Composite Synthesis

The polyol and prepolymer described previously were used to synthesize the composites. The targeted index (the ratio of isocyanate and hydroxyl equivalents multiplied by 100) was 140, and the actual index was calculated from the measured OH number for the polyol and the % NCO calculated for the prepolymer. This value of the index was selected based on previous experiments, which reported that the mechanical properties of compression-molded allograft/PUR composites were optimum at an index of 140. The polyol and the amine catalyst (triethylene diamine) were mixed in a 10 mL cup at 3300 rpm for 1 min using a Hauschild SpeedMixer mixer. The particles were then added and the components hand-mixed for 3 min, followed by addition of the LTI-PEG prepolymer and hand-mixing for another 3 min. The resulting reactive paste was cast into cylindrical molds and a pressure of 330 kPa was applied for a period of time exceeding the setting time of the material. The green composite was subsequently cured at 37° C. for 15 h.

1.2.7. Measurement of Working and Tack-free Times

The working time is defined in the ISO9917 standard as "the period of time, measured from the start of mixing, during which it is possible to manipulate a dental material without an adverse effect on its properties."[9] For a two-component polyurethane, the working time is determined by the gel point, the time at which the crosslink density of the polymer network is sufficiently high that the material gels and no longer flows.[10] The working time was measured by loading the syringe with the reactive composite and injecting <0.25 ml every 30 s. The working time was noted as the time at which the material was more difficult to inject, indicating a significant change in viscosity. For polymeric materials, the tack-free time (TFT) is the time required for the material to cure to form a solid elastomer. Thus the TFT approximates the setting time reported for bone cements, and is defined as the time at which the material could be touched with a spatula with no adhesion of the spatula to the foam. At the TFT, the wound could be closed without altering the properties of the material.

1.2.8. Thermal Analysis

Thermal characterization of a select subset of the composites was performed using the techniques of thermogravimetric analysis (TGA) and differential scanning calorimetry (DSC). The thermal degradation profiles were obtained using a TGA Q500 from TA Instruments. The samples had a mass between 8-10 mg and were heated from 20° C. to 550° C. at a rate of 20° C. min$^{-1}$ under a purge flow of nitrogen. The thermal transitions of the composites were evaluated using a DSC Q200 from T.A. Instruments. Samples with mass between 8 and 12 mg were heated from −50° C. to 120° C. at a rate of 10° C. min$^{-1}$, cooled to −50° C. at a rate of 40° C. min$^{-1}$, and heated again to 120° C. Thermal transitions were analyzed from the second heating cycle.

1.2.9. Mechanical Properties

Compression testing was performed using an MTS 858 Bionix Servohydraulic Test System. Cylindrical specimens (6 mm diameter×12 mm high) were conditioned in PBS at room temperature for 24 h immediately before testing. The specimens were pre-loaded to approximately 12 N, followed by continuous compression until failure at a rate of 25 mm min$^{-1}$. The load and position were recorded every 0.01 s. The compressive stress was calculated by dividing the load by the cross sectional area of the samples and reported in MPa. Young's modulus was calculated as the slope of the initial linear section of the stress-strain curve. The compressive yield point was determined when the load achieved a maximum value after the linear region.

The bonding strength between medical-grade stainless steel (316L) and DFMBP/PUR composites was measured using ASTM D905. Briefly, samples of DFMBP/PUR composites (56.8 vol. % DFMBP) were prepared as described above and the resulting reactive paste was then loaded between two rectangular metal slabs. The sandwich composite was compressed to a constant thickness of 2 mm for 1.5 hrs. The samples were cured at 37° C. for 24 h before the shear strength of the composites was measured. The mode of fracture was determined by Scanning Electron Microscopy (SEM).

1.2.10. Composite Density and Swelling

The height and diameter of the composites were measured with a caliper before and after conditioning the samples in PBS. The samples were weighed and the density was calculated. Swelling was determined from the difference in mass between the samples before and after being conditioned in PBS for 24 hours.

1.2.11. Cell Culture

For cell culture experiments, 11-mm diameter cylinders of selected compositions were cut into thin discs approximately 0.10 mm thick and sterilized by gamma irradiation (25-35 kGy). Next, the samples were conditioned in incomplete culture medium (α-MEM) followed by incubation overnight in complete medium (α-MEM with FBS and antibiotics). 2T3 osteoprogenitor cells were seeded onto the conditioned composites and cultured at 37° C. Viability of the cells seeded on the composites was assessed by Live/Dead staining at 24 and 48 h post-seeding.

Cell proliferation was determined using the CyQuant cell proliferation assay kit on post-seeding days 1, 4 and 7. At each time point, the cells were treated with 1× cell lysis buffer and Cyquant Gr dye (1:400) in the culture wells and incubated at 37° C. for 5 min. A sequence of 3 freeze-thawing cycles was used to remove the cells from the composites and extract their DNA content. Fresh 1× cell lysis buffer/CyQuant Gr dye was added to aliquots of the extracts followed by incubation for 3-5 min. Fluorescence was measured using a FL600 microplate reader at an excitation of 485 nm and emission of 530 nm. The DNA results (ng/ml) were normalized to the area of the materials being tested.

Osteoblast differentiation was analyzed by monitoring the alkaline phosphatase activity of the seeded cells. Two days after the cells were seeded on the composites, the complete media was removed and differentiating media was added to the samples. The differentiating media was composed of α-MEM supplemented with 2.5% FBS, 1% penicillin/streptomycin as well as ascorbic acid (100 μg/mL) and β-Glycerol phosphate (10 mM). Complete media was added to the control wells. The media was changed every 2 days, and the alkaline phosphatase activity was measured on days 2 and 7 after the addition of the differentiating media. Trypsin was used to remove the cells from the disks; a 0.1% TritonX solution in PBS was used to lyse them. The cell lysate was incubated at 37° C. with the Alkaline Phosphatase buffer for 15-30 min. Fluorescence was measured using a FL600 microplate reader at an excitation of 405 nm. A standard curve was prepared with known protein concentrations and used to normalize the results. The controls used for both, the CyQuant and the Alkaline Phosphatase assay, were tissue culture polysterene (empty well plates), glass (12 mm coverslips), and PLGA spin coated coverslips.

1.2.12. Scanning Electron Microscopy (SEM)

The samples analyzed by Scanning Electron Microscopy were gold sputter-coated for 60 seconds. They were analyzed using a Hitachi 2460N Scanning Electron Microscope (Tokyo, Japan). Digital images were obtained using Quartz PCI image management software (Hitachi, Pleasanton, Calif.).

Results

3.1 Characterization of Particles

As shown in Table 1, the density of allograft bone particles was 2.13 g cm$^{-3}$ and did not change significantly after surface-demineralization. Similarly, SEM measurements indicated that the particle size of allograft bone particles (175 μm) did not change after surface-demineralization (data not shown). DFMBP was also reacted with 4-methoxyphenyl isothiocyanate in DMSO at 60° C. in the presence of stannous octoate catalyst. The product was washed with ethanol and lyophilized to remove excess solvent. This reaction aimed to block the free hydroxyl and amine groups on the surface of the filler (Prot. Bone). XPS results for DFMBP, SDMBP, and Prot. Bone are shown in FIG. 1. After surface demineralization, the calcium concentration decreased. This is shown by the increase in the concentrations of carbon, oxygen, and nitrogen relative to the mineral content (FIG. 1) Removal of mineral content is expected to increase the concentrations of proteins at the surface, which is consistent with the reported results.

TABLE 1

Particle size and density of defatted bone particles (DFMBP) and surface demineralized bone particles (SDBMP).

| Particles | Mean size (μm) | Density (g/cm$^3$) |
|---|---|---|
| DFMBP | 175 ± 91 | 2.133 ± 0.002 |
| SDMBP | 175 ± 91 | 2.130 ± 0.009 |

TABLE 2

Surface atomic composition of allograft bone particles as measured by XPS (n = 3).

| Element | DFMBP | SDMBP |
| --- | --- | --- |
| Carbon | 51.6 ± 0.35 | 57.4 ± 2.62 |
| Oxygen | 31.1 ± 0.57 | 25.1 ± 1.98 |
| Phosphorous | 4.5 ± 0.42 | 1.85 ± 0.64 |
| Calcium | 6.75 ± 0.49 | 3.15 ± 0.78 |
| Nitrogen | 6.05 ± 0.07 | 12.6 ± 0.78 |

3.2 Thermal Analysis

Figure 2A:
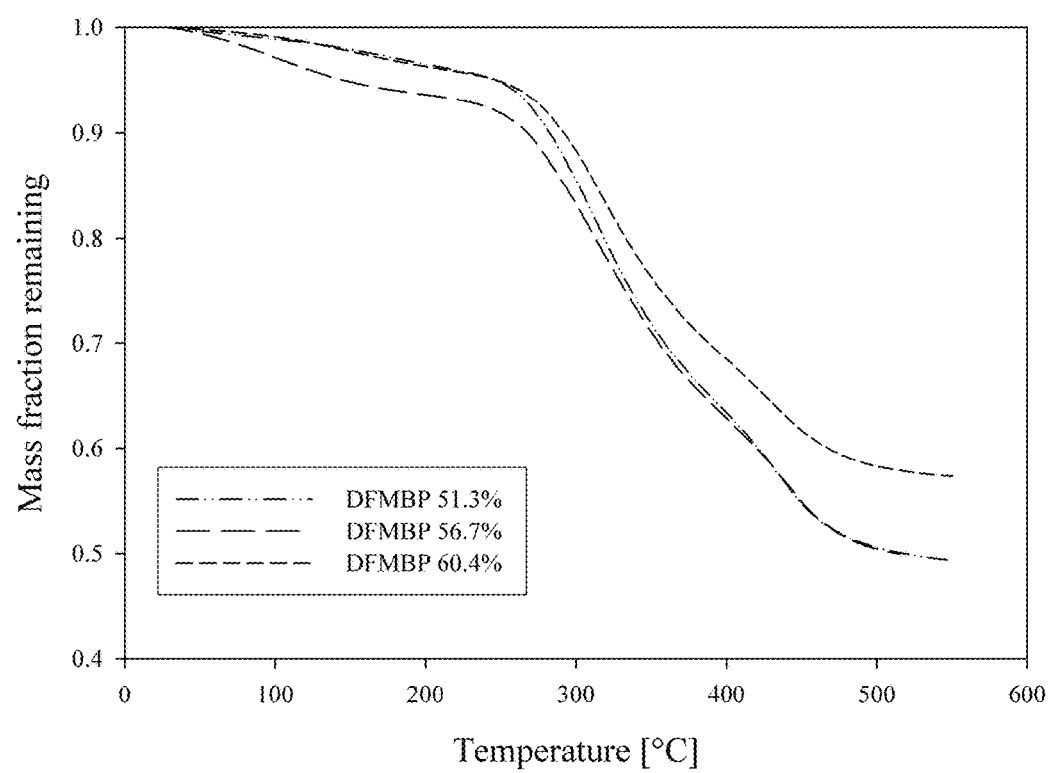
FIG. 2*b*. DSC thermogram of DFMBP/PUR composites.
Figure 2B:
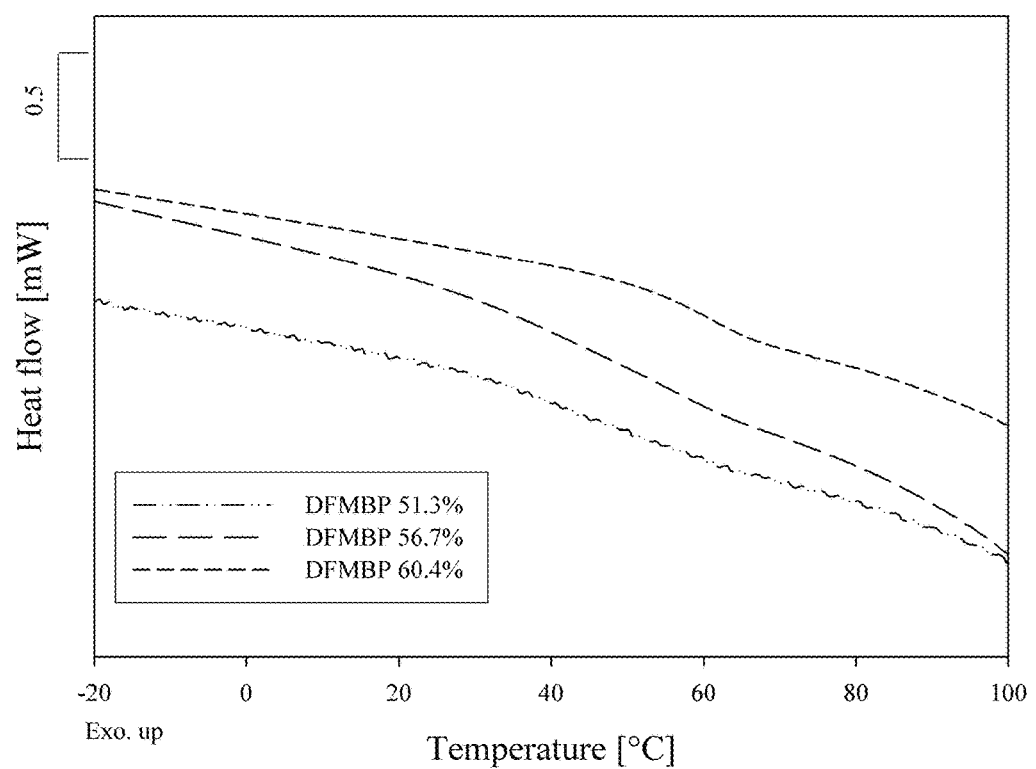

Thermal analysis was performed on samples of DFMBP/PUR composites with three different compositions (51.3%, 56.7%, and 60.4 vol %). The TGA data presented in FIG. 2a show that as low as 50° C., the DFMBP/PUR composites begin to lose mass, which corresponds to dehydration and the degradation of collagen and other extracellular matrix proteins found in bone.[11] The degradation of the polymeric phase takes place between 220° C. and 500°, which agrees with previous results[5]. The DSC thermogram (FIG. 2b) shows that the glass transition temperatures of the DFMBP/PUR composites was 53.4±5.1° C., suggesting that the polyurethane is phase-mixed.[12]

3.3 Compressive Properties and Swelling

Figure 3A:
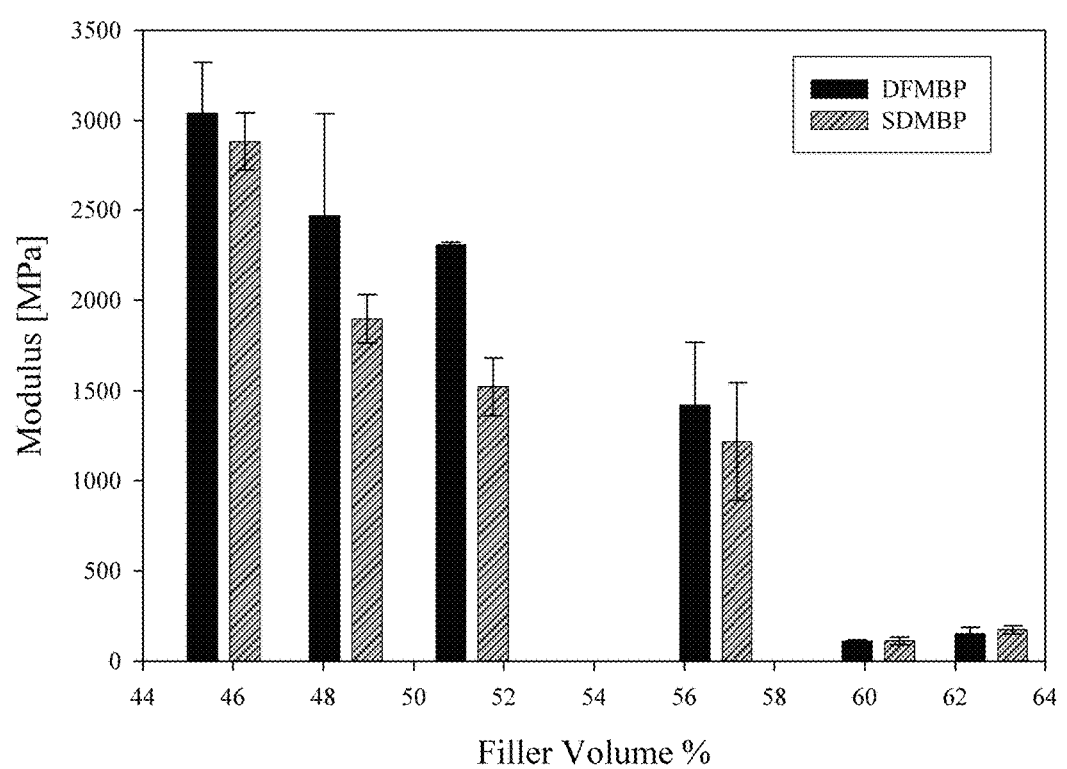
FIG. 3*a*. Compressive modulus of PUR composites with DFMBP and SDMBP as fillers.
Figure 3B:
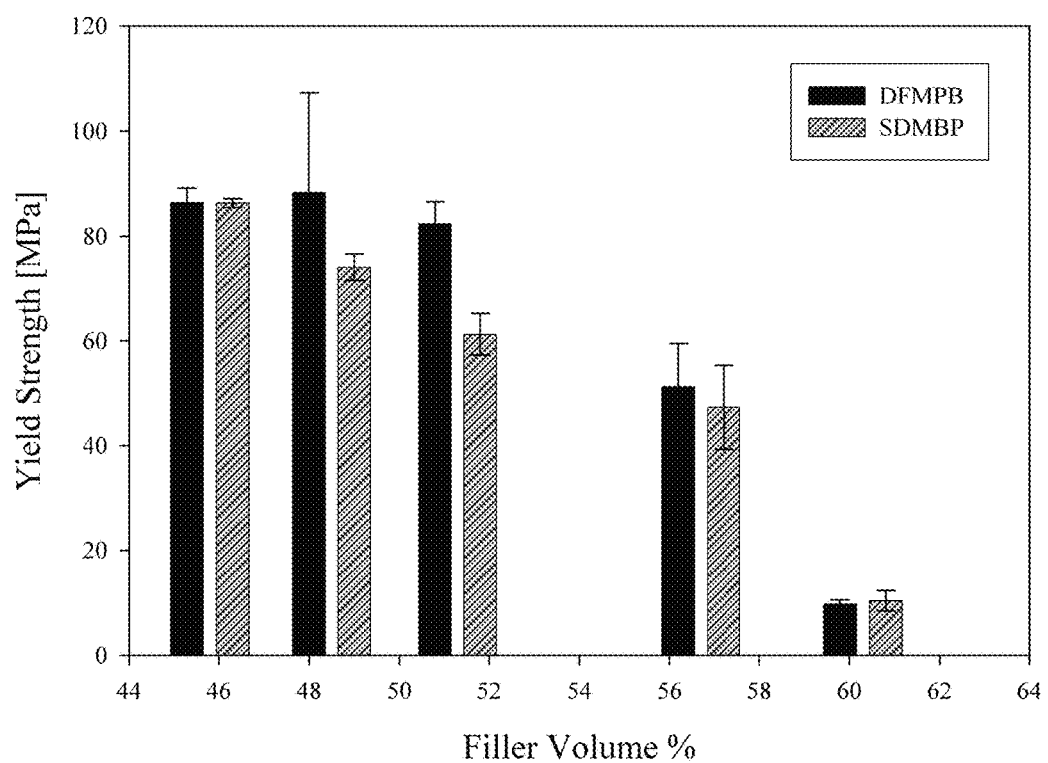
FIG. 3*b*. Compressive strength of PUR composites with DFMBP and SDMBP as fillers.
Figure 3C:
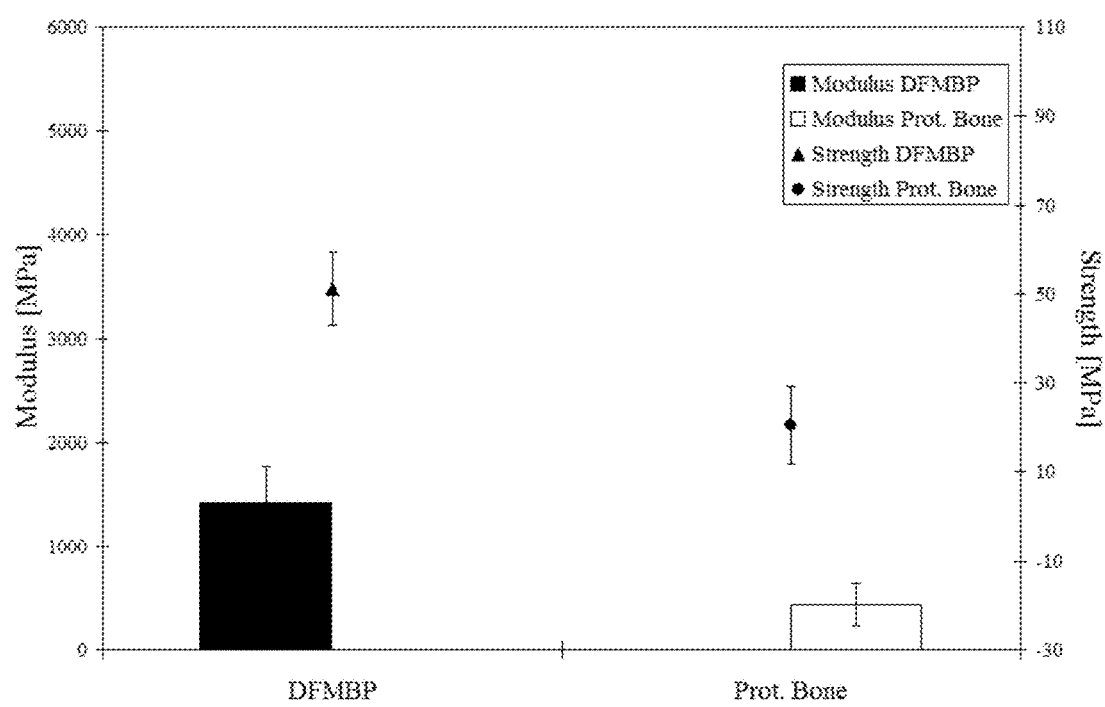
FIG. 3*c*. Compressive modulus and strength of PUR composites with DFMBP and Prot. Bone as fillers.

The compressive modulus and strength of the composites are shown in FIGS. 3a and 3b, respectively. At volume fractions below 0.55, the properties of both DFMBP and SDMBP composites were relatively independent of volume fraction. However, at volume fractions exceeding 0.55 (approaching the random close-packed spheres limit of 0.64), the modulus and strength decreased dramatically. Surprisingly, despite the increase in carbon content at the surface of allograft bone particles after surface-demineralization, composites fabricated from SDMBP had the same, or in some cases lower, mechanical properties as those prepared from DFMBP. Surface-demineralization has been shown to increase the active hydrogen concentration near the surface [13], which was anticipated to enhance interfacial binding and thus the mechanical properties. To investigate the effects of interfacial binding on mechanical properties, composites were prepared from Prot. Bone blocked with unreactive methoxyphenyl isothioscyanate. The compressive strength and moduli of DFMBP and Prot. Bone composites at 56.7 vol % are compared in FIG. 3c. The modulus of the Prot. Bone composites was 437±207 MPa, which is three times smaller than that measured for DFMBP composites (1421±347 MPa). Similarly, the compressive strength of the Prot. Bone composites was 21±8.8 MPa, compared to 51.2±8.2 MPa for DFMBP composites. Taken together, these data suggest that the surface of the allograft particles is reactive toward isocyanates even without surface-demineralization, and that interfacial binding between the allograft and PUR phases is essential for superior mechanical properties.

Figure 4A:
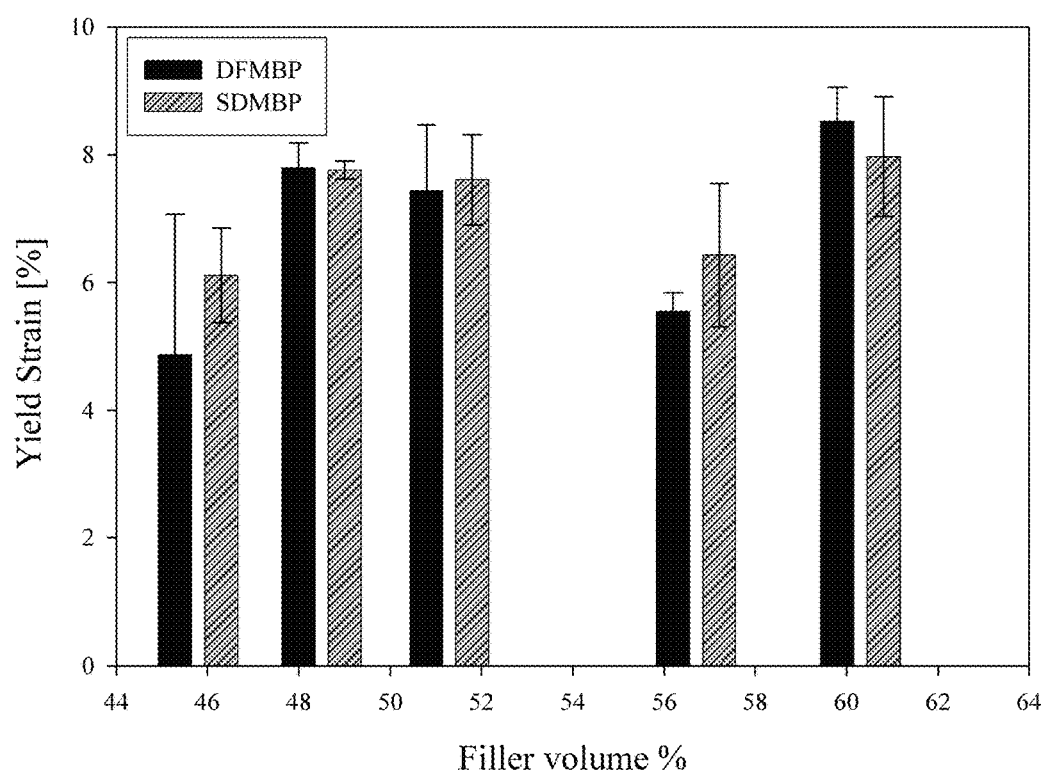
FIG. 4*a*. Compressive yield strain of PUR composites with DFMBP and SDMBP as fillers.
Figure 4B:
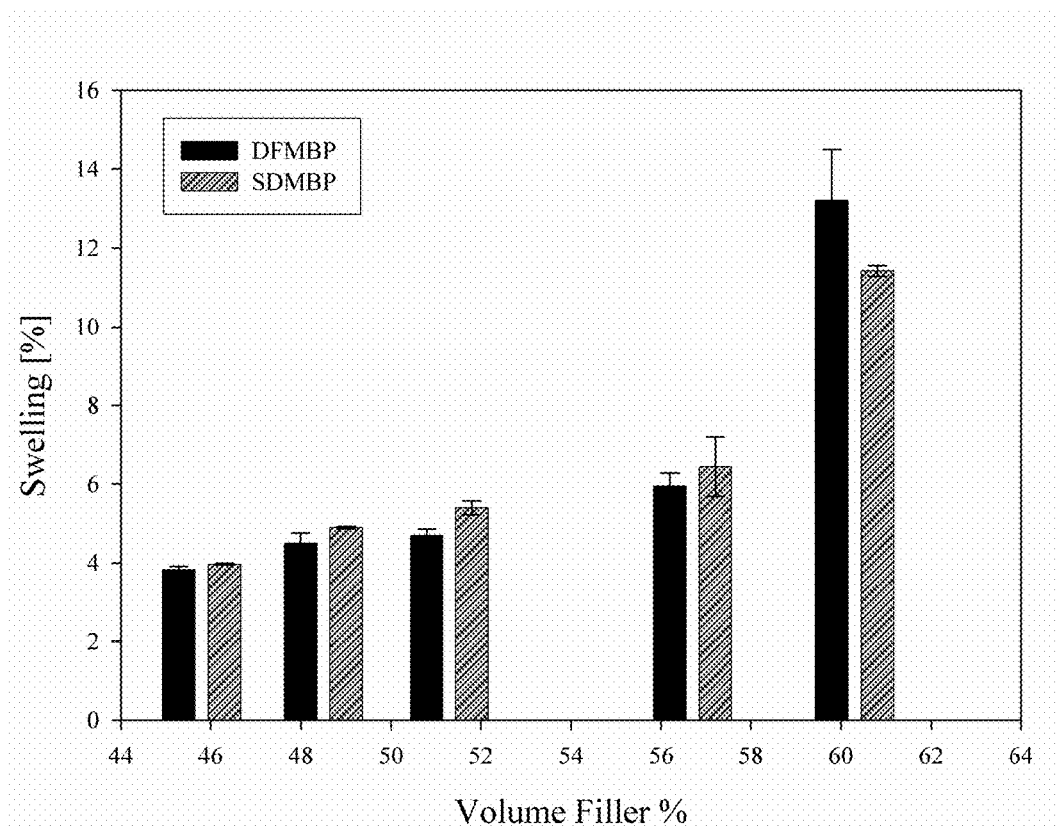
FIG. 4*b*. Swelling of PUR composites with DFMBP and SDMBP as fillers.
Figure 4C:
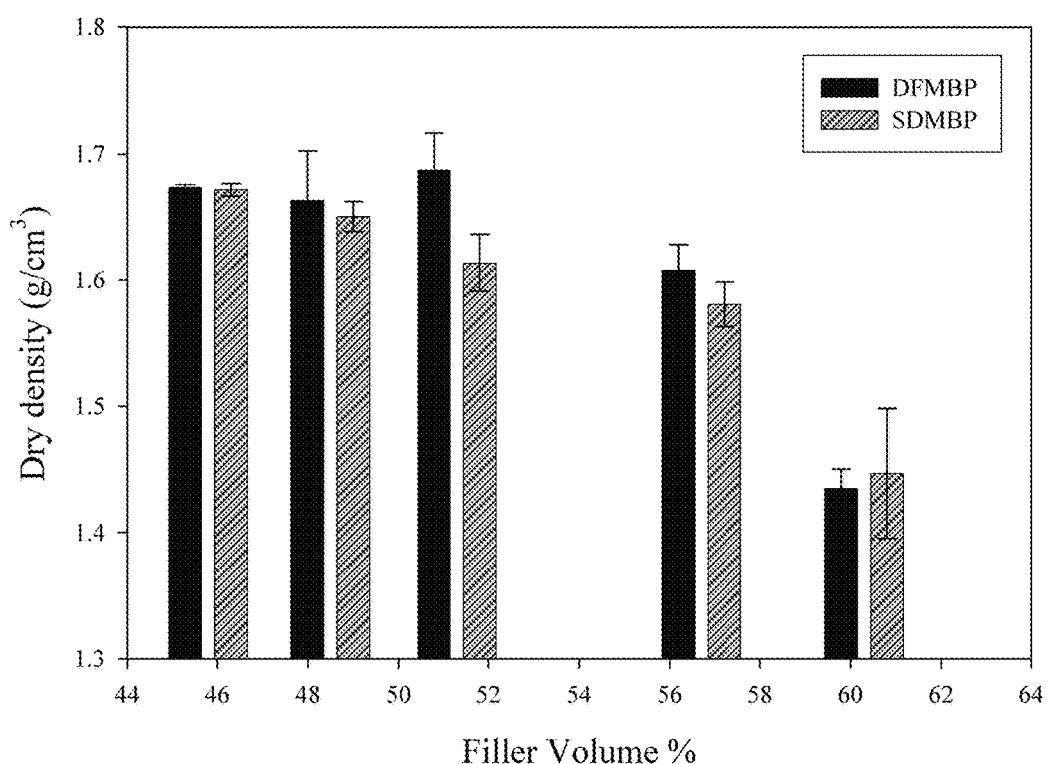
FIG. 4*c*. Density of PUR composites with DFMBP and SDMBP as fillers.

Yield strain, swelling, and density data are presented in FIGS. 4a-c. The yield strain of the DFMB and SDMBP composites did not significantly change over the analyzed range of compositions. As the volume fraction of filler particles exceeds 56%, the swelling increases, presumably due to increasing porosity as the volume fraction of filler approaches the random close-packed limit of 64%. The density data (FIG. 4c) follow a similar trend, exhibiting a significant decrease at volume fractions exceeding 56%. At 56.7 vol % allograft, composites prepared from b-DFMBP exhibited 12.0±0.5% swelling compared to 6.0±0.3% for DFMBP composites.

3.4 Shear Mechanical Properties

The bonding strength between the allograft/PUR composites and 316L stainless steel was measured in order to determine how effectively the composites bind to metal fixation devices. For 56.7 vol % DFMBP composites, the peak load of the shear sandwich was measured to be 356±117.2 N, and the peak stress was measured to be 1.78±0.59 MPa.

References

[1] Tortelli F, Cancedda R. Three-Dimensional Cultures of Osteogenic and Chondrogenic Cells: a Tissue Engineering Approach to Mimic Bone and Cartilage in Vitro. Eur. Cells Mater. 2009; 17:1.

[2] Adhikari R, Gunatillake P A, Griffiths I, Tatai L, Wickramaratna M, Houshyar S, Moore T, Mayadunne R T M, Field J, McGee M, Carbone T. Biodegradable injectable polyurethanes: Synthesis and evaluation for orthopaedic applications. Biomaterials 2008; 29:3762.

[3] Kunze C, Freier T, Helwig E, Sandner B, Reif D, Wutzler A, Radusch H J. Surface modification of tricalcium phosphate for improvement of the interfacial compatibility with biodegradable polymers. Biomaterials 2003; 24:967.

[4] Guelcher S A, Patel V, Gallagher K, Connolly S, Didier J E, Doctor J, Hollinger J O. Synthesis and biocompatibility of polyurethane foam scaffolds from lysine diisocyanate and polyester polyols. Tissue Eng 2006; 12:1247.

[5] Guelcher S A, Srinivasan A, Dumas J E, Didier J E, McBride S, Hollinger J O. Synthesis, mechanical properties, biocompatibility, and biodegradation of polyurethane networks from lysine polyisocyanates. Biomaterials 2008; 29:1762.

[6] Guelcher S, Srinivasan A, Hafeman A, Gallagher K, Doctor J, Khetan S, McBride S, Hollinger J. Synthesis, In vitro degradation, and mechanical properties of two-component poly(ester urethane)urea scaffolds: Effects of water and polyol composition. Tissue Eng. 2007; 13:2321.

[7] Dumas J E, Zienkiewicz K, Tanner S, Prieto E M, Battacharyya S, Guelcher S A. Synthesis and Characterization of an Injectable Allograft Bone/polymer Composite Bone Void Filler with Tunable Mechanical Properties. Tissue Eng. 2009;Submitted.

[8] Marotti G, Muglia M A. A scanning electron microscope study of human bony lamellae. Proposal for a new model of collagen lamellar organization. Archivio Italiano di Anatomia e di Embriologia 1988; 93:163.

[9] Clarkin O M, Boyd D, Madigan S, Towler M R. Comparison of an experimental bone cement with a commercial control, Hydroset™. J Mater Sci: Mater Med 2009; 20:1563

[10] Sperling L H. Introduction to Physical Polymer Science. New York: Wiley-Interscience, 2001.

[11] Dumas J E, Davis T E, Yoshii T, Nyman J, Holt G E, Perrien D S, Boyce T M, Guelcher S A. Synthesis of Allograft Bone/Polymer Composites and Evaluation of Remodeling in a Rabbit Femoral Condyle Model. Acta Biomaterialia 2010; In Press, Uncorrected Proof:doi: 10.1016/j.actbio.2010.01.030.

[12] Hafeman A, Li B, Yoshii T, Zienkiewicz K, Davidson J, Guelcher S. Injectable biodegradable polyurethane scaffolds with release of platelet-derived growth factor for tissue repair and regeneration. Pharm Res 2008; 25:2387.

[13] Dumas J E, Davis T, Holt G E, Yoshii T, Perrien D, Nyman J, Boyce T, Guelcher SA. Synthesis, Characterization, and Remodeling of Weight-bearing Allograft Bone/Polyurethane

Example 2

Figure 5:
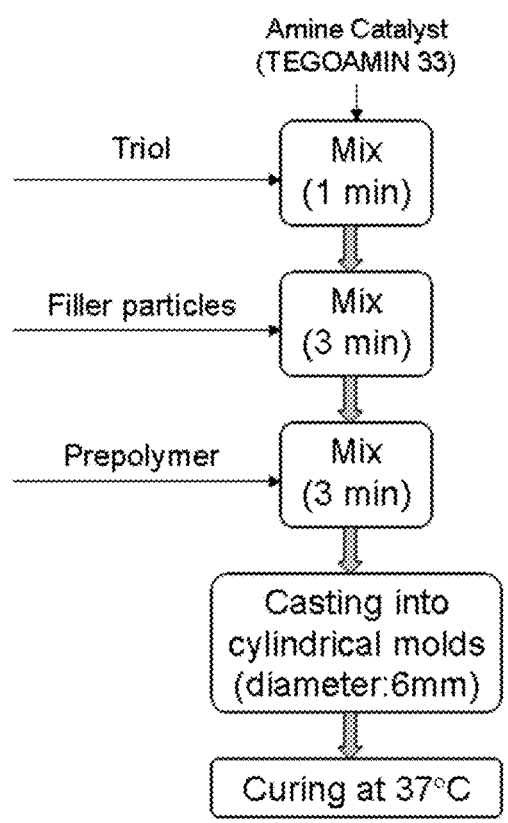
FIG. 5. Mixing procedure to synthesize filler/PUR composites
Figure 6:
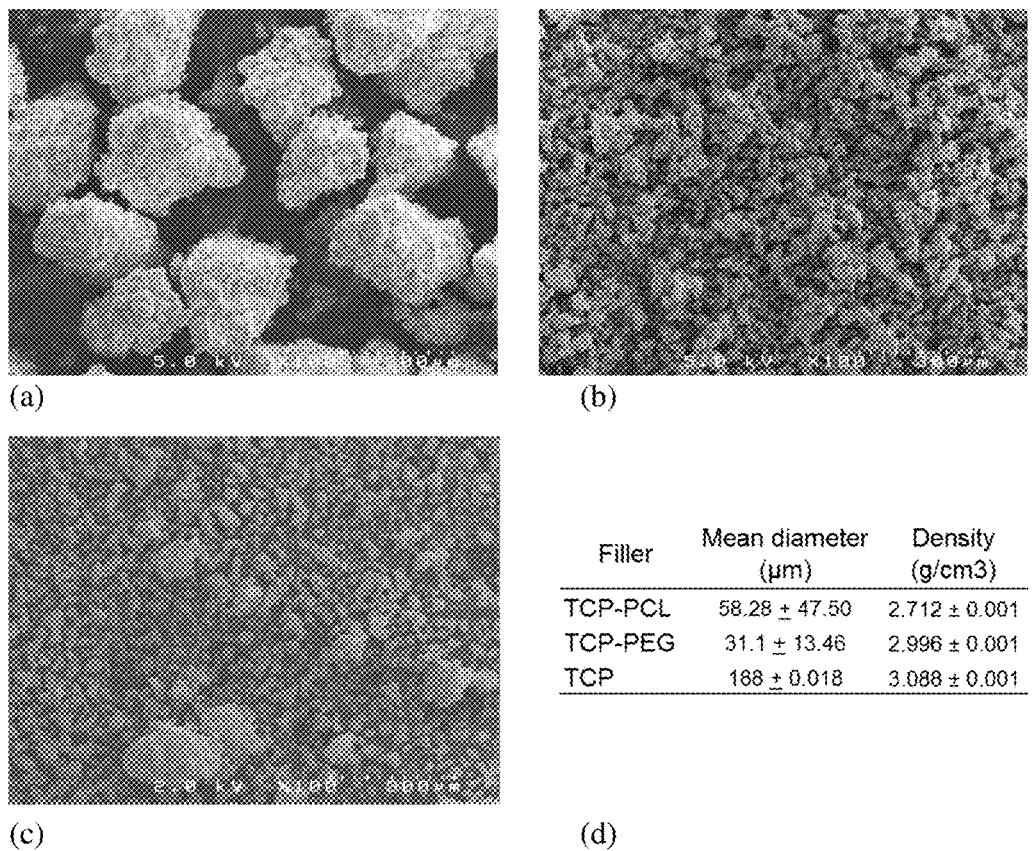
FIG. 6. Particle size of TCP, TCP-PEG, and TCP-PCL. Scanning electron micrographs of a) TCP, b) TCP-PEG, c) TCP-PCL. d) Particle size was determined from the SEM images using Metamorph. Density was measured using gas pycnometry (Micromeritics).
Figure 7:
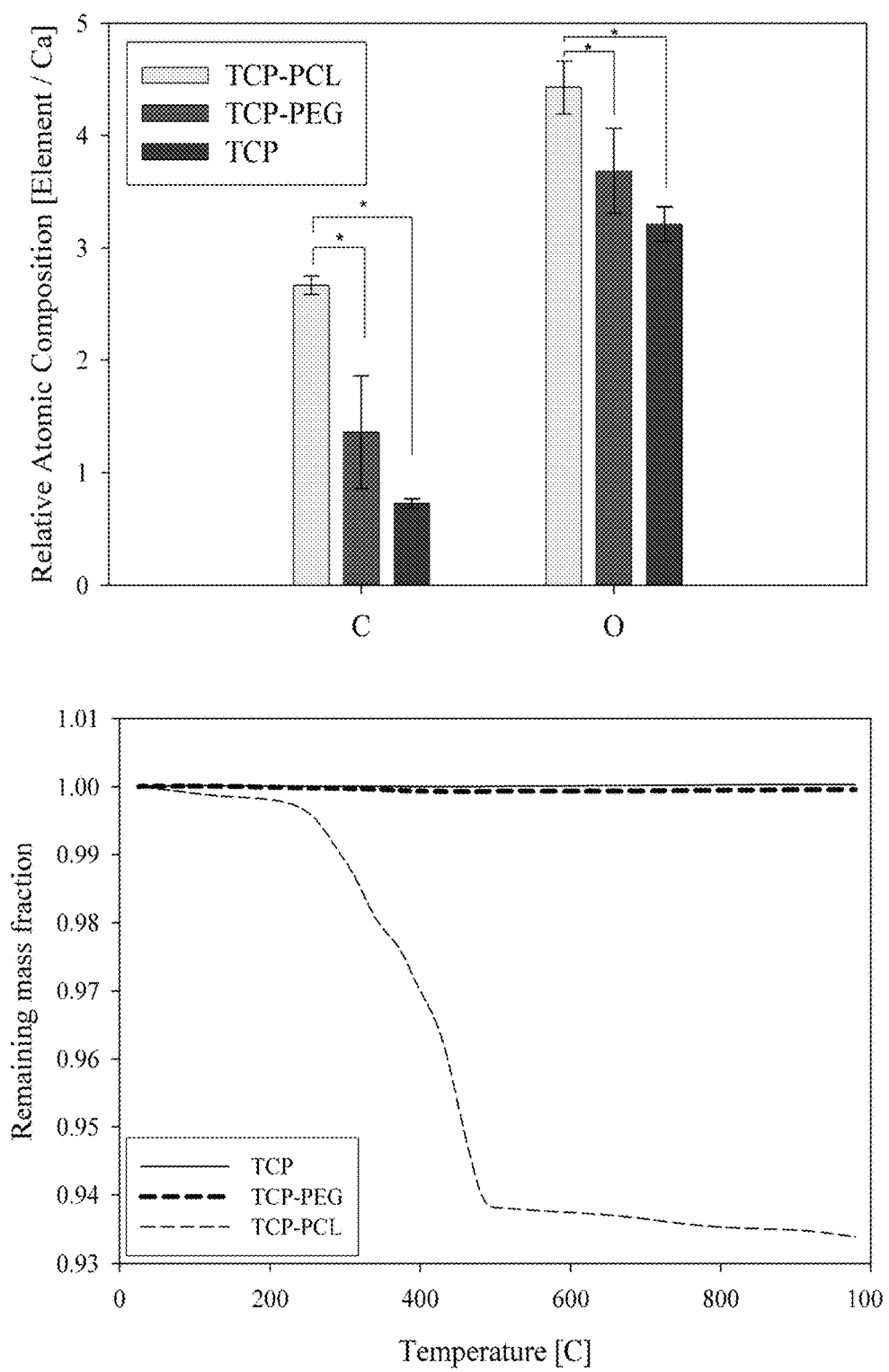
FIG. 7. Characterization of TCP, TCP-PEG and TCP-PCL fillers. a) XPS. Pellets of the samples were analyzed in a PHI 5000 VersaProbe with a 25 W monochromatic Al K-α X-ray. The atomic percentages were normalized to Calcium in the mineral phase. (All groups had at least 3 samples) b) TGA using a TA Q500.
Figure 8:
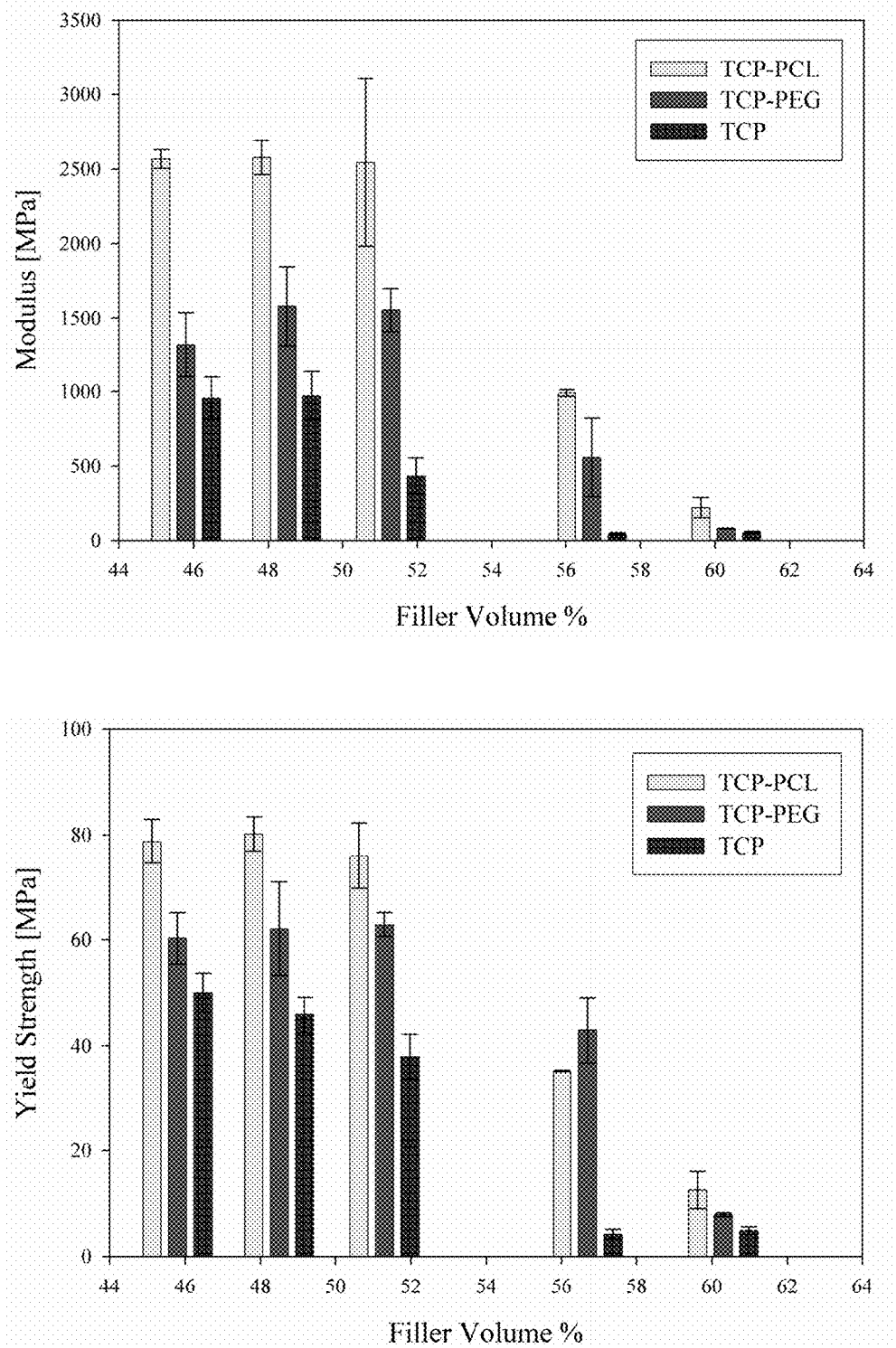
FIG. 8. Compressive modulus and strength of DFMBP/PUR and SDMBP/PUR composites. Compression testing was completed on wet cylindrical samples with 6 mm diameter and approximate height of 12 mm using an MTS 858 Bionix Servohydraulic Test System.

Surface modification of β-tricalcium phosphate (TCP) favors the attachment between the PUR and filler phase in modified-TCP/PUR composites. In this work we studied the integration of TCP and modified-TCP particles into the PUR matrix. TCP (Berkeley Advanced Biomaterials) has grain size distribution 100-300 um, an average particle size of 188±0.018 um and a density of 3.088±0.001 g cm$^{-3}$ (measured by gas pycnometry—Micromeritics). Ceramic biomaterials, such as TCP, offer biocompatibility and osteoconductivity but have brittle mechanical properties. TCP/PUR composites were fabricated according to FIG. 5, and the mechanical properties were between 42-97% lower than those of DFMBP/PUR composites in the filler content range studied. The low compressive modulus and strength limit the applications of TCP/PUR composites as bone scaffolds. Two surface modification methods were studied to increase the interaction between the PUR and TCP phases: i) adsorption of PEG at the surface of TCP (TCP-PEG), ii) covalent grafting of polycaprolactone (PCL) to the surface of TCP (TCP-PCL). The hydroxyl groups of PEG and PCL can react with the isocyanate groups and bind the filler to the PUR phase. Polyethylene glycol (PEG, 8000 MW, Alfa Aesar) was adsorbed on the surface of TCP by incubating a 5% suspension of TCP in PEG for 5 h followed by filtering and drying under vacuum at 80° C. PCL was covalently grafted to TCP particles by stirring with 5% aqueous phosphoric acid for 1 h, followed by washing and vacuum-drying; the resulting protonated material was then reacted with ε-caprolactone at 150° C. for 4 days. The molar ratio of TCP to ε-caprolactone was 1:10, which has been reported to generate PCL with molecular weight of 1100 g/mol. The product (TCP-PCL) was washed with chloroform, filtered, and dried under vacuum at 40° C. for 15 h. Analysis of scanning electron micrographs (SEM) of the TCP-filler particles (FIG. 6, a-c) revealed a significant ($P<0.001$) decrease in particle size after the surface modification treatments (FIG. 6, d). To evaluate if the TCP modifications had taken place on the TCP surface, XPS analysis of the surface and thermogravimetric analysis (TGA—TA Instruments Q500) were completed. XPS results (FIG. 7, a) showed a significant ($P<0.05$) increase in C/Ca ratio on the surface of TCP-PCL filler compared to TCP and TCP-PEG. This increase in carbon content on the surface is evidence of the grafting of PCL to the surface of TCP. TGA data (FIG. 7, b) suggests that 6.6 wt % of the TCP-PCL filler corresponds to grafted PCL. The ceramic component of the filler is stable in the temperature range of the experiment as evidenced by the curve corresponding to TCP; any change in mass is attributed to the degradation of polymer chains. XPS and TGA results indicate that no effective adsorption of PEG on the surface of TCP is taking place. The improvement in mechanical properties (FIG. 8) of the TCP-PEG composites compared to the TCP composites can be attributed to the reduced particle size of the fillers. Since there is no significant ($P<0.05$) difference between the particle size of TCP-PEG and TCP-PCL, the increase in mechanical properties of the TCP-PCL composites (FIG. 8) can be attributed to higher filler-matrix interactions although this conjecture requires additional evidence (see Research plan, Sp. Aim 1). The grafting of PCL on the surface of TCP improved the compressive modulus of the TCP/PUR composites from 63 to 96% depending on the filler composition; the compressive strength improved from 36 to 88% (FIG. 8). These improvements are higher than the 28% increase in strength reported in the literature for a surface-modified biphasic calcium phosphate/poly(L-lactide) composite (mBCP/PLLA), or the lack of improvement in mechanical properties in surface-modified TCP/PLLA composites. In these two cases the modified filler was mixed with the PLLA phase, while with the materials developed in this study the fillers were covalently incorporated into the PUR network. From these results it can be concluded that in the fabrication of PUR composites the use of TCP particles with PCL grafted covalently at the surface produces materials with mechanical properties suitable for various biomedical applications.

Figure 9:
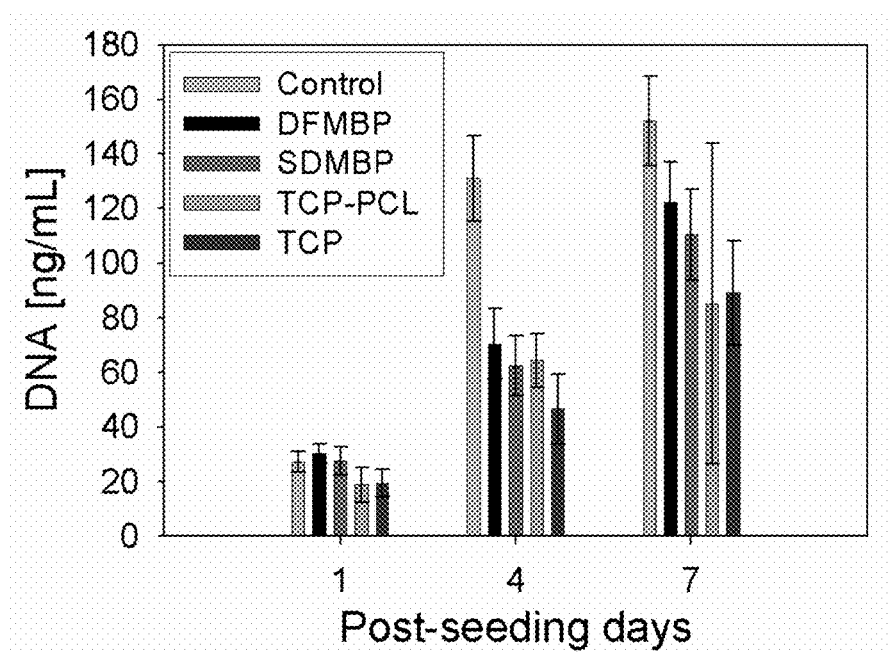
FIG. 9. Proliferation of MC3T3 on the composite materials with a filler content of 56.7% vol. The control data refers to cells cultured on tissue culture plastic. DNA standards included in the kit were used to calibrate the fluorescence readings.

PUR composites filled with DFMBP, SDMBP, TCP, and TCP-PCL are biocompatible and support cellular proliferation. 6 mm disks of the modified-filler/PUR composites, with thickness <1 mm were sterilized with ethanol and conditioned in complete media (□-MEM, 10% FBS, 1% Penicillin-Streptomycin) overnight. $1\times10^4$ osteoblast-like cells (MC3T3) were seeded on each sample in 48-well tissue culture polysterene plates and cultured with complete media. Cell viability was assessed using the Live/Dead Viability/Cytotoxicity staining kit (Invitrogen). After 2 days of culture ≥95% of the cells were viable on all of the composites (results not shown). Proliferation of MC3T3 cells was monitored using the Cyquant Cell Proliferation Assay Kit (Invitrogen) on post-seeding days 1, 4 and 7. At each time point, the cells were removed from the samples with trypsin treatment and frozen in a pellet at −80° C. According to the results presented in FIG. 9, all the modified-filler/PUR composites supported cell proliferation from day 1 to day 7. However, the composite materials presented a lower proliferation rate than the controls. An observation leading to lower DNA content in the composites compared to the controls was related to difficulties in the seeding process: not all the cells landed on the samples and instead went to the bottom of the well. A possible option to eliminate this variation is to mold the samples directly in the well. Future testing will be conducted with this procedure. The above results show that osteoblast-like cells can attach and proliferate on the modified-filler/PUR composites. Adsorption of PEG and grafting of PCL increased the fraction of carbon on the surface and decreased the amount of calcium and phosphorus, indicating that the polymers were successfully bound to the surface of the β-TCP.

Example 3

The components of Plexur LV are defatted sieved bone (particle size 100-500 μm), dipropylene glycol (DPG), water, a tri-functional poly (caprolactone-glycolide-lactide) copolymer (900 Mw polyol), triethylene diamine (catalyst) and Lysine triisocyanate-poly (ethylene glycol) prepolymer (774 Mw). For the analysis of the Plexur LV system, each individual component was examined as a unique reaction with the isocyanate component. This allowed for the calculation of a rate constant for each component. With this information a better understanding of the total reaction can be elucidated. In order to ensure accurate measurements, the catalyst was kept at a constant molar ratio with the isocyanate prepolymer.

Figure 10:
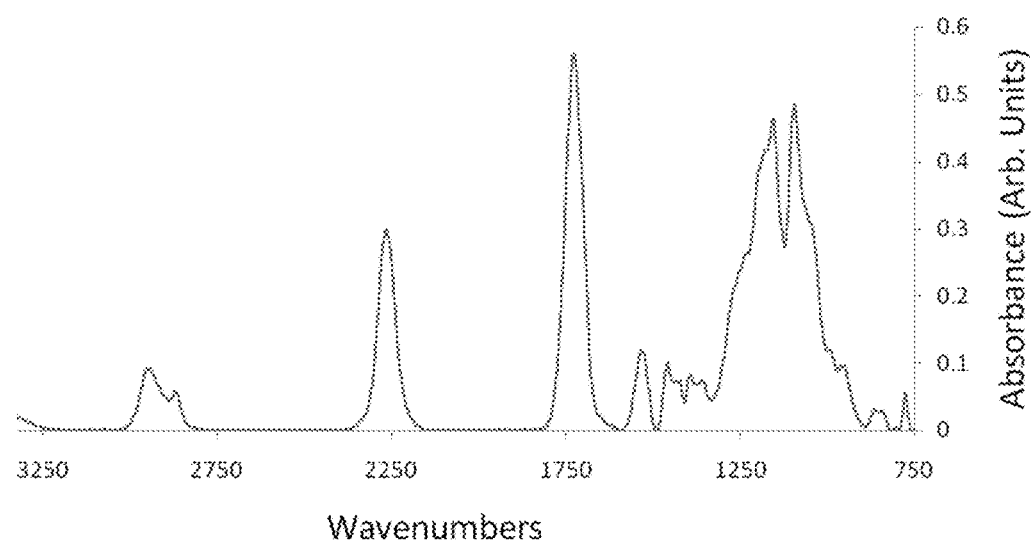
FIG. 10. General spectra seen with the reacting Plexur LV system.

A Seagull ATR (Manufactured by Harrick Scientific) apparatus was utilized in a Bruker Tensor 27 FTIR to take each measurement. The Seagull ATR kit provides a hemispherical ZnSe crystal which focuses the IR beam onto a sample. As long as intimate contact is maintained with the sample and crystal, thickness of the sample does not matter. A standard sample spectra for the reacting Plexur LV system is shown in FIG. 10. This snapshot is at a time before all of the isocyanate is converted to urethane or urea. The peaks of interest are the isocyanate peak (2270 cm$^{-1}$) and the carbonyl peak (1750 cm$^{-1}$). The kinetic rates of the reactions can be found by measuring the size of the isocyanate peak with respect to time. Time zero plots were obtained by diluting the prepolymer in the same ratio as the reaction mixture, but without catalyst.

In order to obtain quantitative data from the ATR setup a calibration curve must be obtained. In this instance the calibration curve was obtained by diluting the isocyanate prepolymer in DPG without catalyst added. The area of the isocyanate peak was tracked as a function of dilution. This allowed for a relation of molar concentration to absorbance. This was adjusted to just give the molar concentration of purely the NCO functionality by using the NCO number of the prepolymer. The resulting linear trend was utilized to obtain the rate constants for each of the individual components except water. The reaction with water will be explained in more detail later.

The reaction of isocyanate with polyol and DPG is very similar. The main difference is that the polyol is composed of three primary hydroxyl moieties while DPG is a mixture of isomers with either primary or secondary hydroxyl's present. These reactions follow the rate equation shown in equation 1.

$$\text{Rate} = k[\text{NCO}][\text{OH}] \qquad (1)$$

Figure 11:
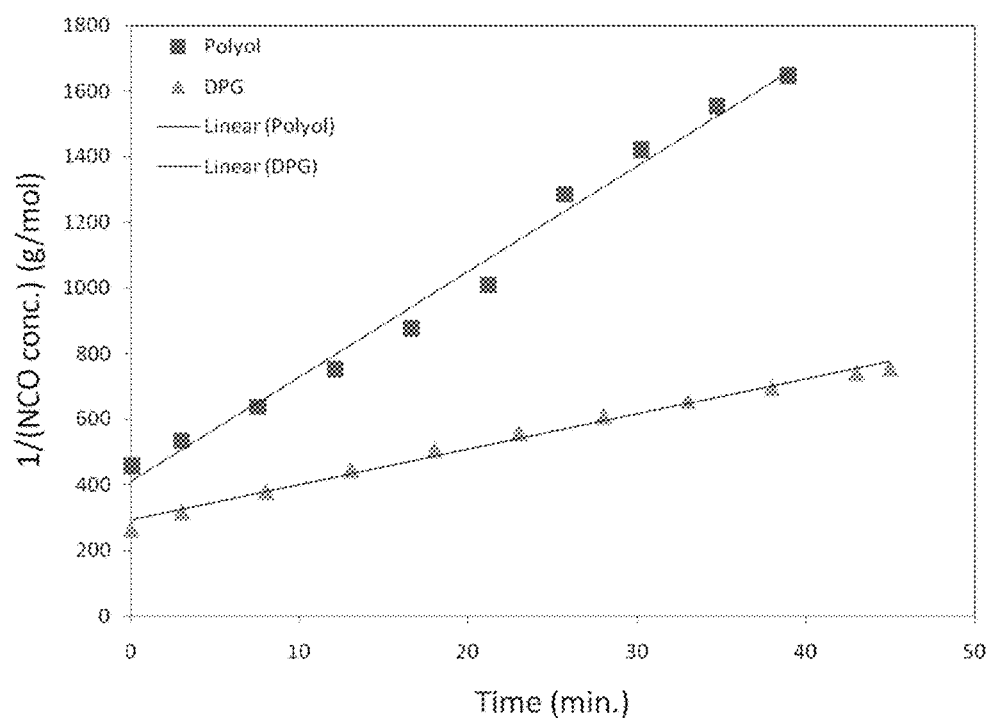
FIG. 11. The inverse of the concentration of NCO units plotted with respect to time for polyol and DPG reactions with the isocyanate prepolymer.

The area of the isocyanate peak was tracked with respect to time. The area was converted to a concentration and the inverse of the concentration was plotted with respect to time. The data along with a linear fit of the results are shown in FIG. 11.

Figure 12:
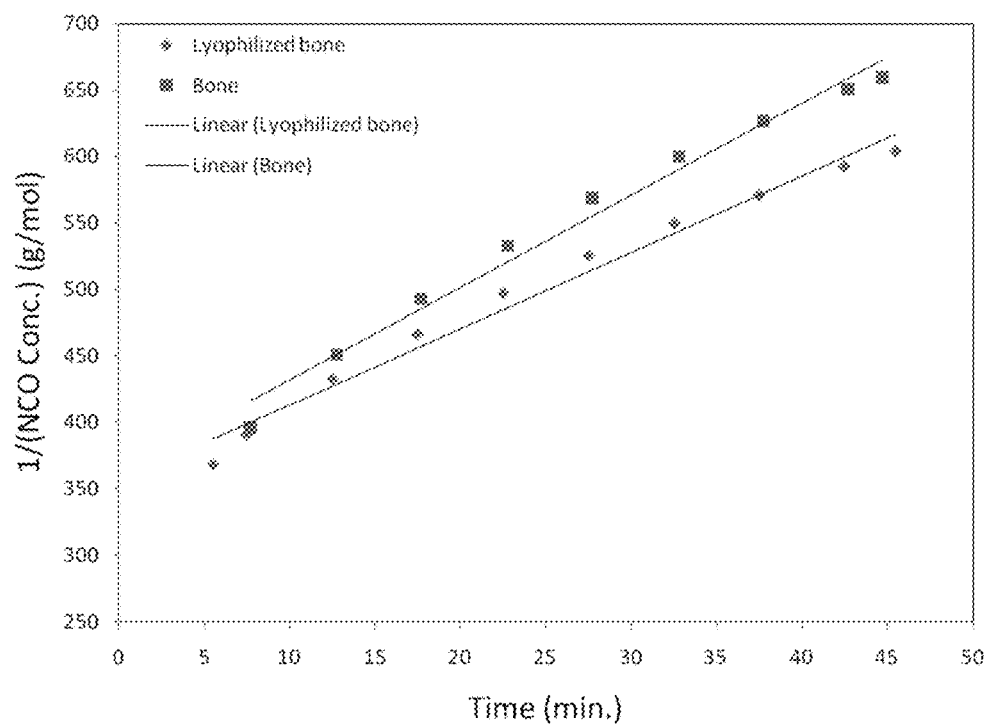
FIG. 12. The inverse of the concentration of NCO units plotted with respect to time for stored and lyophilized bone reactions with the isocyanate prepolymer.

The reaction with of isocyanate and bone is also slightly more complex than the simple reaction shown in equation 1. As of now, the total amount of functionalities for bone is unknown, but it is known that there are primary hydroxyl's present on the surface of the bone. These hydrophilic moiety can attract water. The amount of bound water depends on how the bone is treated and stored. Lyophilization can reduce the amount of bound water to 3%, while bone stored in air can accumulate up to 5% bound water. Water bound to the surface can cause a quick reaction with the isocyanate. This is demonstrated in a quick drop in isocyanate concentration, followed by a more subdued decrease. After the majority of the bound water is reacted, the remaining isocyanate can react with the bones hydroxyl units. A linear plot is observed if early time points are neglected. Two rate experiments were completed for bone. One sample was lyophilized directly prior to analysis, while the later was taken from storage. The resulting kinetic profiles, shown in FIG. 12, were obtained. There is a slight difference between the two rates, but the significance is not known.

Figure 13:
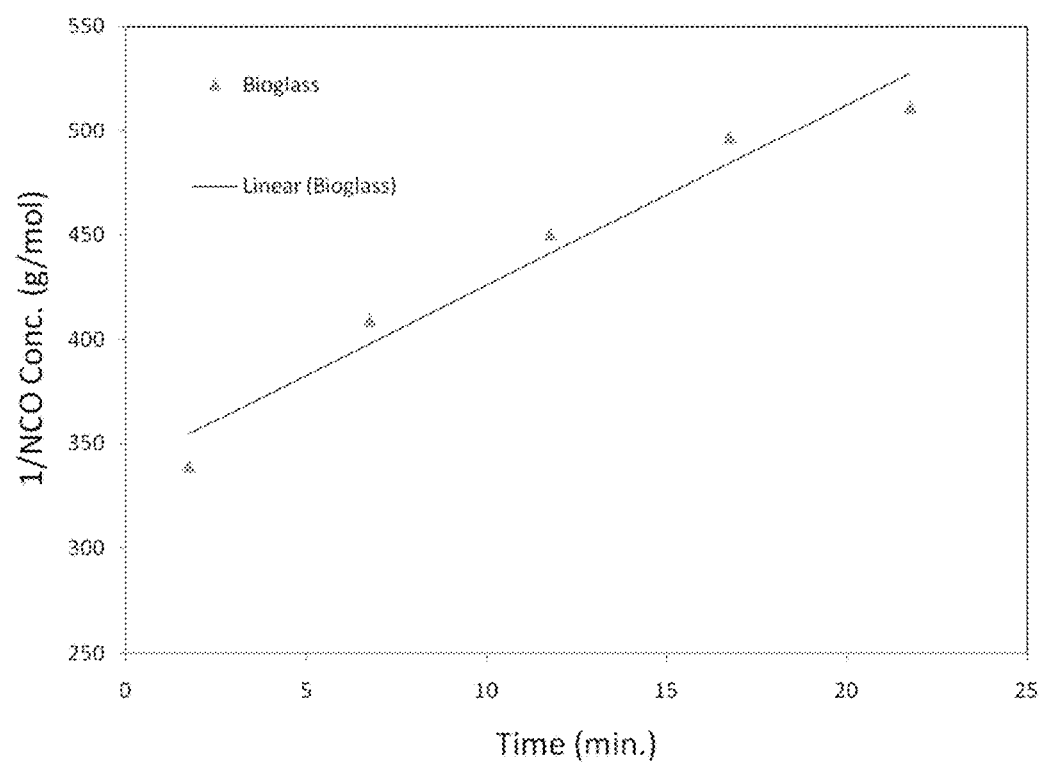
FIG. 13. The inverse of the concentration of NCO units plotted with respect to time for Bioglass reactions with the isocyanate prepolymer.

In an attempt to place a range of reaction rates for the purpose of the patent application, Bioglass was used as an upper bound. In earlier experiments Bioglass has shown to produce quick working times that limited its usefulness for this specific application. The kinetic profile is shown in FIG. 13. The rate constant is closer to that of DPG. The fit of the experimental data for each of the above kinetic profiles is >0.95. Kinetic rates for these reactions, with the exception of water, is summarized in Table 3.

TABLE 3

Kinetic rates for each individual components reaction with the isocyanate prepolymer.

| Component | Rate (g mol$^{-1}$ sec$^{-1}$) |
|---|---|
| Water | 92.6 |
| Polyol | 32.1 |
| DPG | 10.7 |
| Lyophilized Bone | 5.7 |
| Bone | 6.9 |
| Bioglass | 8.6 |

The reaction of isocyanate and water is a very vigorous reaction. In order to observe the reaction on a feasible timescale, DPG was used to dilute the water. DPG reacts much slower than water and therefore would not impede the waters affinity for the prepolymer. The kinetic profile for water does not fit the second order model shown in equation 1. Instead an autocatalytic model (taken from Chemical Reaction Engineering, 3$^{rd}$ Ed.) was proposed that provides a better fit, shown in equation 2.

$$\frac{\ln((1 + Xa))}{(1 - Xa)} \qquad (2)$$

where Xa is the conversion of the isocyanate group and C is the concentration of isocyanate.

Figure 14:
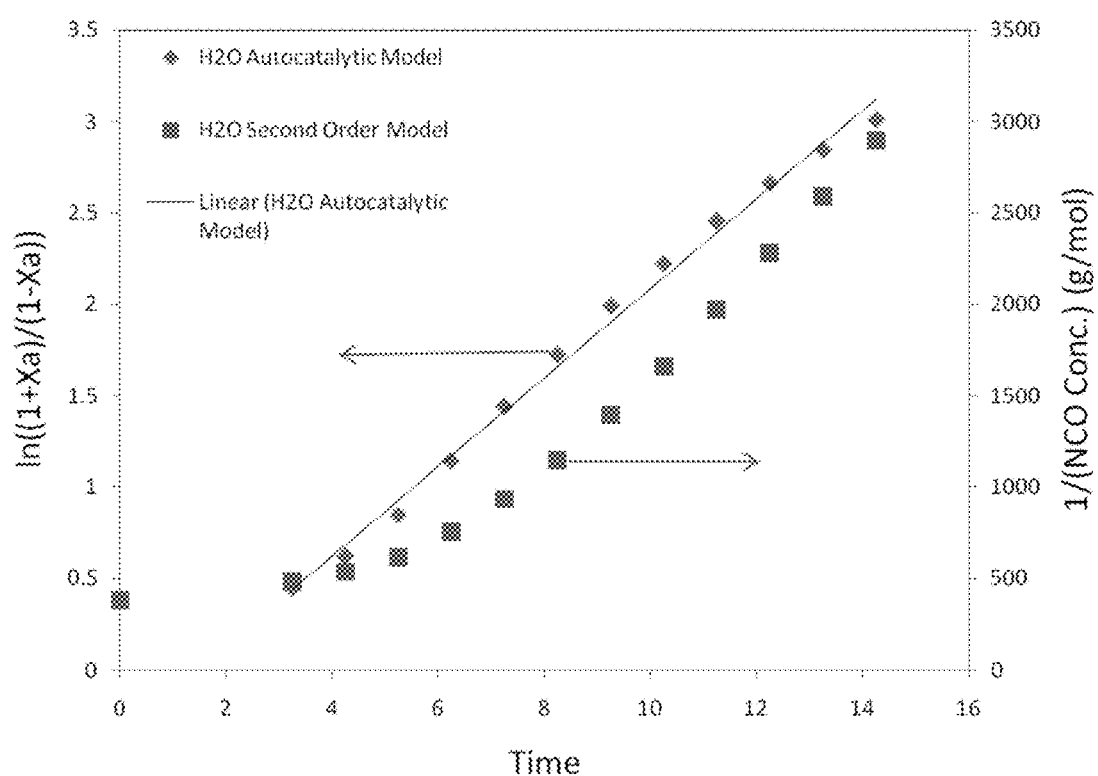
FIG. 14. The inverse of the concentration of NCO units plotted with respect to time for water reaction with the isocyanate prepolymer (red); Plot of experimental data fit with the autocatalytic model (blue).

FIG. 14 displays a comparison of the second order and autocatalytic models for the kinetic profile of the water and isocyanate reaction. The second order model is non-linear. This model is not an accurate model for this reaction. The autocatalytic model fits the data very well. The slope of this linear curve is equal to the initial concentration of the isocyanate multiplied by the rate constant.

Example 4

Figure 15:
FIG. 15 mCT images of allograft/PUR composites injected into a 6×11 mm plug defect in the femoral condyle of NZW rabbits. Residual allograft particles are distinguished by their irregular shape and sharp corners. The images show evidence of allograft resorption and new bone formation.
Figure 15:
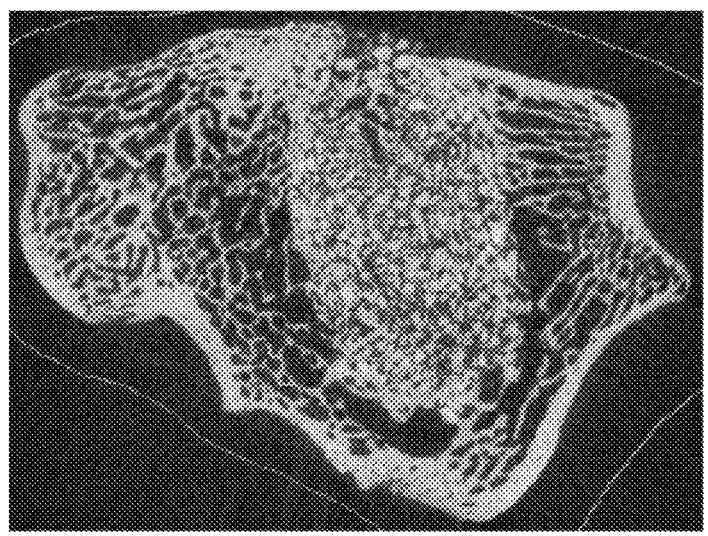

In preliminary experiments we have investigated the remodeling of allograft/PUR composites injected into 6×11 mm plug defects in the femoral condyle of NZW rabbits. The settable putty was prepared from a lysine triisocyanate (LTI)-polyethylene glycol (PEG) prepolymer, polyester polyol, defatted allograft bone particles (DFMBP), and triethylene diamine (TEDA) catalyst in a dipropylene glycol (DPG) carrier. The polyester polyol backbone was composed of 60% caprolactone, 30% glycolide, and 10% lactide and had a molecular weight of 900 g mol$^{-1}$ (6C3G1L900). Polyol, DFMBP, catalyst solution, and LTI-PEG prepolymer were added to a mixing cup and mixed for 90 seconds. The filler content (DFMBP) was maintained constant at 70 wt % for each treatment group. The resulting paste was then mixed for 60 seconds. Bilateral plug defects approximately 6 mm in diameter by 11 mm in depth were drilled in the metaphysis of the distal femurs of each rabbit. DFMBP/PUR putty from each treatment group was injected into the defects. The setting time was approximately 10 minutes. After 6 or 12 weeks, the rabbits were sacrificed and the femurs removed. Faxitron LX-60 X-ray and mCT40 systems were used to acquire images of the femurs. The wet (i.e., after 24 h incubation in saline) compressive strength of the composites cured in vitro ranged from 27.2 to 33.2 MPa. FIG. 15 shows 2D mCT scans of the composites at each time point. The images reveal evidence of allograft resorption and new bone formation in all treatment groups due to creeping substitution of the allograft component (appearing as large, dense, irregularly shaped white particles in the images) in the center of the composite. These data suggest that the low-porosity allograft/PUR composite remodels in a femoral plug defect without the formation of large resorption gaps.

After fixation, the femurs were embedded in Technovit 7200 and 200-um sections were cut from the resulting blocks using an Exakt band saw. The sections were then ground and polished using an Exakt grinding system to less than 100 um and stained with Sanderson's rapid bone stain counterstained with van Gieson. Old allograft bone stained light brown, while new bone stained pink with dark blue osteocytes within the matrix. The polymer was stained dark blue, while cells were stained light blue. Ground histological sections at 6 and 12 weeks implantation time are shown in Figures X and Y, respectively. Low magnification (2×) view show new bone formation and remodeling near the surface of the implant. High magnification views (20×) show new bone (NB) formation (red) and infiltration of cells (C, blue), as well as residual allograft (A, dark red) and polymer (P, black). By 12 weeks, almost all of the polymer had resorbed.

All references, such as patents, patent applications, and publications, referred to above are incorporated by reference in their entirety.

Other embodiments are within the scope of the following claims.

What is claimed is:

1. A composition comprising:
a polyurethane material, said polyurethane comprising a NCO-terminated prepolymer, the NCO-terminated prepolymer comprising a polyisocyanate that includes about 10 wt % to about 55 wt % NCO and a first polyol that includes a molecular weight of about 100 g/mol to about 500 g/mol, and a second polyol that reacts with said polyisocyanate; and
a treated particulate ceramic biomaterial;
wherein the first polyol has a functionality of not more than two; and
wherein the second polyol has a functionality of two or more.

2. The composition of claim 1, wherein the particulate ceramic biomaterial comprises an inorganic material.

3. A composition comprising:
a polyurethane material including a NCO-terminated prepolymer comprising a lysine triisocyanate having about 10 wt % to about 55 wt % NCO; and, a particulate material that does not comprise bone; wherein the particulate material contains a plurality of surface-reactive moieties available to form interactions with the polyurethane material.

4. The composition of claim 3 wherein the particulate material comprises an inorganic material.

5. The composition of claim 4, wherein the inorganic material is selected from the group consisting of aragonite, dahlite, calcite, amorphous calcium carbonate, vaterite, weddellite, whewellite, struvite, urate, ferrihydrite, francolite, monohydrocalcite, magnetite, goethite, dentin, calcium carbonate, calcium sulfate, calcium phosphosilicate, sodium phosphate, calcium aluminate, calcium phosphate, hydroxyapatite, α-tricalcium phosphate, β-tricalcium phosphate, dicalcium phosphate, 3-tricalcium phosphate, tetracalcium phosphate, amorphous calcium phosphate, octacalcium phosphate (OCP), calcium phosphate silica glass, fluoroapatite, chloroapatite, magnesium-substituted tricalcium phosphate, carbonate hydroxyapatite, and combinations thereof.

6. The composition of claim 3, wherein the particulate material is associate with a polymer.

7. The composition of claim 6, wherein the polymer is absorbed or grafted on the particulate material.

8. The composition of claim 6, wherein the polymer is PEG and/or polycaprolactone (PCL).

9. The composition of claim 1, further comprising one or more of serum albumin, collagen, an extracellular matrix component, a synthetic polymer, and a naturally-derived polymer.

10. The composition of claim 1, wherein the polyurethane material comprises an additional polymer selected from the group consisting of poly(caprolactones), poly(lactide), poly(glycolide), polyglyconate, poly(arylates), poly(anhydrides), poly(hydroxy acids), polyesters, poly(ortho esters), poly(alkylene oxides), polycarbonates, poly(propylene fumarates), poly(propylene glycol-co fumaric acid), polyamides, polyesters, polyethers, polyureas, polyamines, polyamino acids, polyacetals, poly(orthoesters), poly(pyrolic acid), poly(glaxanone), poly(phosphazenes), poly(organophosphazene), polylactides, polyglycolides, poly(dioxanones), polyhydroxybutyrate, polyhydroxyvalyrate, polyhydroxybutyrate/valerate copolymers, poly(vinyl pyrrolidone), polycyanoacrylates, polyurethanes, polysaccharides, and combinations thereof.

11. The composition of claim 1, wherein the polyurethane material comprises poly(caprolactone), poly(lactide), poly(glycolide), and/or combinations thereof.

12. The composition of claim 3, wherein the polyurethane material comprises poly(caprolactone-co-lactide-co-glycolide),
wherein a percentage of caprolactone in the polyol ranges from approximately 10% to 60%;
wherein a percentage of lactide in the polyol ranges from approximately 10% to approximately 80%; and
wherein a percentage of glycolide in the polyol ranges from approximately 10% to approximately 60%.

13. The composition of claim 1, wherein the polyurethane material comprises a poly(ethylene glycol) (PEG).

14. The composition of claim 1, wherein the polyurethane material is resorbed within approximately 4 weeks to approximately 8 weeks.

15. The composition of claim 1, wherein the polyurethane material is resorbed within approximately 2 months to approximately 6 months.

16. The composition of claim 1, wherein the polyurethane material is resorbed within approximately 6 months to approximately 12 months.

17. The composition of claim 1, further comprising a catalyst.

18. The composition of claim 17, wherein the catalyst is selected from the group consisting of an organometallic, an organobismuth, bis(2-demethylaminoethyl)ether (DMAEE), triethylene diamine (TEDA), stannous octoate, dibutyltin dilaurate, and iron acetylacetonate.

19. The composition of claim 1, further comprising a bioactive agent.

20. The composition of claim 19, wherein the bioactive agent is selected from the group consisting of antiviral agent, antimicrobial agent, antibiotic agent, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, anti-rejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, and penetraction enhancer.

21. The composition of claim 19, wherein the bioactive agent is an antibiotic agent.

22. The composition of claim 1, being configured for the repair of a simple fracture, compound fracture or non-union; as an external fixation device or internal fixation device; for joint reconstruction, arthrodesis, arthroplasty or cup arthroplasty of the hip; for femoral or humeral head replacement; for femoral head surface replacement or total joint replacement; for repair of the vertebral column, spinal fusion or internal vertebral fixation; for tumor surgery; for deficit filling; for discectomy; for laminectomy; for excision of spinal tumors; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; for revision surgery; for revision surgery of a total joint arthroplasty; and for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones or metatarsal bones.

23. The composition of claim 1, wherein the particulate ceramic biomaterial comprises at least one of hydroxyapatite or β-tricalcium phosphate.

24. The composition of claim 1, wherein the particulate ceramic biomaterial comprises calcium phosphate silica glass.

25. The composition of claim 4, wherein the particulate material comprises calcium phosphate silica glass.

26. The composition of claim 1, wherein the surface of the particulate ceramic biomaterial is grafted with a polymer to bond with said polyurethane material.

27. The composition of claim 1, wherein the surface of the particulate ceramic biomaterial is grafted with a silane to bond with the polyurethane material.

28. The composition of claim 2, wherein the inorganic material is selected from the group consisting of aragonite, dahlite, calcite, amorphous calcium carbonate, vaterite, weddellite, whewellite, struvite, urate, ferrihydrite, francolite, monohydrocalcite, magnetite, goethite, dentin, calcium carbonate, calcium sulfate, calcium phosphosilicate, sodium phosphate, calcium aluminate, calcium phosphate, hydroxyapatite, α-tricalcium phosphate, β-tricalcium phosphate, dicalcium phosphate, 3-tricalcium phosphate, tetracalcium phosphate, amorphous calcium phosphate, octacalcium phosphate (OCP), calcium phosphate silica glass, fluoroapatite, chloroapatite, magnesium-substituted tricalcium phosphate, carbonate hydroxyapatite, and combinations thereof.

29. The composition of claim 17, wherein the catalyst is iron acetylacetonate.

30. The composition of claim 3, further comprising one or more of serum albumin, collagen, an extracellular matrix component, a synthetic polymer, and a naturally-derived polymer.

31. The composition of claim 3, wherein the polyurethane material comprises an additional polymer selected from the group consisting of poly(caprolactones), poly(lactide), poly(glycolide), polyglyconate, poly(arylates), poly(anhydrides), poly(hydroxy acids), polyesters, poly(ortho esters), poly(alkylene oxides), polycarbonates, poly(propylene fumarates), poly(propylene glycol-co fumaric acid), polyamides, polyesters, polyethers, polyureas, polyamines, polyamino acids, polyacetals, poly(orthoesters), poly(pyrolic acid), poly(glaxanone), poly(phosphazenes), poly(organophosphazene), polylactides, polyglycolides, poly(dioxanones), polyhydroxybutyrate, polyhydroxyvalyrate, polyhydroxybutyrate/valerate copolymers, poly(vinyl pyrrolidone), polycyanoacrylates, polyurethanes, polysaccharides, and combinations thereof.

32. The composition of claim 3, wherein the polyurethane material comprises poly(caprolactone), poly(lactide), poly(glycolide), and/or combinations thereof.

33. The composition of claim 3, wherein the polyurethane material comprises a poly(ethylene glycol) (PEG).

34. The composition of claim 33, wherein the PEG has an average molecule weight in a range of approximately 100 to 500 g/mol.

35. The composition of claim 3, wherein the polyurethane material is resorbed within approximately 4 weeks to approximately 8 weeks.

36. The composition of claim 3, wherein the polyurethane material is resorbed within approximately 2 months to approximately 6 months.

37. The composition of claim 3, wherein the polyurethane material is resorbed within approximately 6 months to approximately 12 months.

38. The composition of claim 3, further comprising a catalyst.

39. The composition of claim 38, wherein the catalyst is selected from the group consisting of an organometallic, an organobismuth, bis(2-demethylaminoethyl)ether (DMAEE), triethylene diamine (TEDA), stannous octoate, dibutyltin dilaurate, and iron acetylacetonate.

40. The composition of claim 3, further comprising a bioactive agent.

41. The composition of claim 40, wherein the bioactive agent is selected from the group consisting of antiviral agent, antimicrobial agent, antibiotic agent, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, anti-rejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, and penetraction enhancer.

42. The composition of claim 40, wherein the bioactive agent is an antibiotic agent.

43. The composition of claim 1, wherein the polyisocyanate is lysine triisocyanate.

44. The composition of claim 1, wherein the first polyol and the second polyol are different.

* * * * *